(12) United States Patent
Heidebrecht et al.

(10) Patent No.: US 8,759,579 B2
(45) Date of Patent: Jun. 24, 2014

(54) CYCLOBUTYL SULFONES AS NOTCH SPARING GAMMA SECRETASE INHIBITORS

(75) Inventors: Richard W. Heidebrecht, Brookline, MA (US); Chaomin Li, Boston, MA (US); Benito Munoz, Newtonville, MA (US); Andrew Rosenau, Philadelphia, PA (US); Laura M. Surdi, Collegeville, PA (US); Paul Tempest, Brookline, MA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 756 days.

(21) Appl. No.: 12/989,131

(22) PCT Filed: Apr. 17, 2009

(86) PCT No.: PCT/US2009/040913
§ 371 (c)(1),
(2), (4) Date: Oct. 22, 2010

(87) PCT Pub. No.: WO2009/131906
PCT Pub. Date: Oct. 29, 2009

(65) Prior Publication Data
US 2011/0039925 A1    Feb. 17, 2011

Related U.S. Application Data

(60) Provisional application No. 61/125,212, filed on Apr. 23, 2008.

(51) Int. Cl.
*C07C 311/13* (2006.01)
*C07C 61/16* (2006.01)
*A61K 31/195* (2006.01)
*A61K 31/18* (2006.01)

(52) U.S. Cl.
USPC .............. 564/97; 514/460; 514/562; 514/605

(58) Field of Classification Search
USPC .............................. 564/97; 514/460, 562, 605
See application file for complete search history.

(56) References Cited

U.S. PATENT DOCUMENTS
2007/0203120 A1    8/2007    McDevitt et al.

FOREIGN PATENT DOCUMENTS
| WO | 02081435 A1 | 10/2002 |
| WO | 2004031139 A1 | 4/2004 |
| WO | 2005030709 A1 | 4/2005 |

OTHER PUBLICATIONS

Best, et al., vol. 317, No. 2, pp. 786-790, 2006.
Best, et al., J. Pharmacol. Exp. Ther., 320:552-558, 2007.

*Primary Examiner* — Sikarl Witherspoon
(74) *Attorney, Agent, or Firm* — J. Eric Thies; John C. Todaro

(57) ABSTRACT

The invention encompasses a novel class of cyclobutyl sulfone derivatives which inhibit the processing of APP by the putative γ-secretase while sparing Notch signaling pathway, and thus are useful in the treatment or prevention of Alzheimer's disease without the development of Notch inhibition mediated gastrointestinal issues. Pharmaceutical compositions and methods of use are also included.

14 Claims, 4 Drawing Sheets

MRK-560:

Example 2:

CYCLOBUTYL SULFONES AS NOTCH SPARING GAMMA SECRETASE INHIBITORS

BACKGROUND OF THE INVENTION

The present invention relates to a novel class of compounds, their salts, pharmaceutical compositions comprising them and their use in therapy of the human body. In particular, the invention relates to novel cyclobutyl sulfone derivatives which inhibit the processing of APP by γ-secretase, and hence are useful in the treatment or prevention of Alzheimer's disease. The compounds of the invention also spare the Notch signaling pathway. As such, the compounds of the invention are believed to halt or potentially reverse the progression of Alzheimer's disease without the development of toxicities mediated by Notch inhibition.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by a progressive loss of memory and cognitive function, and pathologically characterized by the deposition of extracellular proteinaceous plaques in the cortical and associative brain regions of sufferers. These plaques are mainly comprised of fibrillar aggregates of β-amyloid peptide (Aβ) (Glenner G G and Wong C W (1984) Alzheimer's disease: Initial report of the purification and characterization of a novel cerebrovascular amyloid protein. Biochemical and Biophysical research Communications. 120(3); 885-890). The role of secretases, including that of γ-secretase, in the processing of amyloid precursor protein (APP) to form Aβ is well documented in the literature. Aβ is generated by proteolytic processing of APP by two enzymes, β-amyloid cleavage enzyme (BACE) and γ-secretase (FIG. 1; Selkoe D J (2001) Alzheimer's disease: genes, proteins, and therapy. Physiological Review. 81(2):741-766). γ-Secretase is a complex comprised of four proteins: presenilin (presenilin-1 or -2), nicastrin, APH-1 and PEN-2 (Takasugi N, Tomita T, Hayashi I, Tsuruoka M, Niimura M, Takahashi Y, Thinakaran G, Iwatsubo T (2003) The role of presenilin cofactors in the gamma-secretase complex. Nature. 422(6930):438-441; Kimberly W T, LaVoie M 3, Ostaszewski B L, Ye W, Wolfe M S, Selkoe D J (2003) Gamma-secretase is a membrane protein complex comprised of presenilin, nicastrin, Aph-1, and Pen-2. Proceedings of the National Academy of Sciences. 100 (11):6382-6387; Edbauer D, Winkler E, Regula J T, Pesold B, Steiner H, Haass C (2003) Reconstitution of gamma-secretase activity. Nature Cell Biology. 5(5):486-488.). Presenilin-1 and -2 contain transmembrane aspartyl residues that have been shown to be essential for the catalytic activity of the complex (Wolfe M S, Xia W, Ostaszewski B L, Diehl T S, Kimberly W T, Selkoe D J (1999) Two transmembrane aspartates in presenilin-1 required for presenilin endoproteolysis and gamma-secretase activity. Nature. 1999 398(6727):513-517). The majority of the mutations linked to the early onset, familial form of AD (FAD) are associated with either PS-1 or PS-2 (Scheuner D, Eckman C, Jensen M, Song X, Citron M, Suzuki N, Bird T D, Hardy J, Hutton M, Kukull W, Larson E, Levy-Lahad E, Viitanen M, Peskind E, Poorkaj P, Schellenberg G, Tanzi R, Wasco W, Lannfelt L, Selkoe D, Younkin S (1996) Secreted amyloid beta-protein similar to that in the senile plaques of Alzheimer's disease is increased in vivo by the presenilin 1 and 2 and APP mutations linked to familial Alzheimer's disease. Nature Medicine. 2(8):864-870; Duff K, Eckman C, Zehr C, Yu X, Prada C M, Perez-tur J, Hutton M, Buee L, Harigaya Y, Yager D, Morgan D, Gordon M N, Holcomb L, Refolo L, Zenk B, Hardy J, Younkin S (1996) Increased amyloid-beta42(43) in brains of mice expressing mutant presenilin 1. Nature. 383(6602):710-713; Lemere C A, Lopera F, Kosik K S, Lendon C L, Ossa J, Saido T C, Yamaguchi H, Ruiz A, Martinez A, Madrigal L, Hincapie L, Arango J C, Anthony D C, Koo E H, Goate A M, Selkoe D J, Arango J C (1996) The E280A presenilin 1 Alzheimer mutation produces increased A beta 42 deposition and severe cerebellar pathology. Nature Medicine. 2(10):1146-1150; Citron M, Westaway D, Xia W, Carlson G, Diehl T, Levesque G, Johnson-Wood K, Lee M, Seubert P, Davis A, Kholodenko D, Motter R, Sherrington R, Perry B, Yao H, Strome R, Lieberburg I, Rommens J, Kim S, Schenk D, Fraser P, St George Hyslop P, Selkoe D J (1997) Mutant presenilins of Alzheimer's disease increase production of 42-residue amyloid beta-protein in both transfected cells and transgenic mice. Nature Medicine. 3(1):67-72). γ-Secretase processes a number of other type I membrane proteins that have undergone a prerequisite ectodomain shedding (Lleó A (2008) Activity of gamma-secretase on substrates other than APP. Current Topics in Medicinal Chemistry. 8(1):9-16).

In addition to processing APP, γ-secretase cleaves the Notch family of receptors. Genetic evidence indicates that γ-secretase activity is critically required for Notch signaling and functions (Shen J, Bronson R T, Chen D F, Xia W, Selkoe D J, Tonegawa S (1997) Skeletal and CNS defects in Presenilin-1-deficient mice. Cell. 89(4):629-639; Wong P C, Zheng H, Chen H, Becher M W, Sirinathsinghji D J, Trumbauer M E, Chen H Y, Price D L, Van der Ploeg L H, Sisodia S S (1997) Presenilin 1 is required for Notch1 and DII1 expression in the paraxial mesoderm. Nature. 387(6630):288-292). Notch is an evolutionarily conserved and widely expressed single-span type I transmembrane receptor that plays a prominent role in regulating cell fate decisions in the developing embryo (Artavanis-Tsakonas S, Rand M D, Lake R J (1999) Notch signaling: cell fate control and signal integration in development. Science. 284(5415):770-776). The role of Notch in the adult remains unclear but Notch proteins are expressed in various adult tissues and are thought to play a role in regulating stem cell differentiation. Four Notch genes have been identified in mammals (Notch 1-4); all four Notch proteins are cleaved by γ-secretase (Saxena M T, Schroeter E H, Mumm J S, Kopan R (2001) Murine notch homologs (N1-4) undergo presenilin-dependent proteolysis. Journal of Biological Chemistry. 276(43):40268-40273). Notch activation is induced by binding, in trans, to the Delta/Serrate/LAG2 family of transmembrane ligands. Notch signal transduction is mediated by three cleavage events: (a) cleavage at Site 1 in extracellular domain; (b) cleavage at Site 2 just N-terminal to the extracellular/transmembrane domain boundary following ligand binding; and (c) cleavage at Site 3 (S3) within the transmembrane near the transmembrane/cytoplasmic domain boundary. Site 3 cleavage is required for release of Notch intracellular domain (NICD) and is mediated by γ-secretase (Schroeter E H, Kisslinger J A, Kopan R (1998) Notch-1 signalling requires ligand-induced proteolytic release of intracellular domain. Nature. 393(6683):382-386). NICD activates transcription mediated by the (CSL) CBF1/Serrate/LAG-1 family of DNA binding proteins and induces expression of various genes. NICD-regulated transcription is thought to be a key component of Notch-mediated signal transduction.

The development of γ-secretase inhibitors to block APP cleavage and Aβ generation is hampered by the potential for mechanism-based toxicity due to inhibition of Notch processing. Notch-related toxicities have been observed in studies where animals have been dosed subchronically with γ-secretase inhibitors. Intestinal goblet cell metaplasia is consistently observed following three or more days of treatment (Searfoss G H, Jordan W H, Calligaro D O, Galbreath E J, Schirtzinger L M, Berridge B R, Gao H, Higgins M A, May P C, Ryan T P (2003) Adipsin, a biomarker of gastrointestinal toxicity mediated by a functional gamma-secretase inhibitor. Journal of Biological Chemistry. 278(46):46107-46116; Wong G T, Manfra D, Poulet F M, Zhang Q, Josien H, Bara T, Engstrom L, Pinzon-Ortiz M, Fine J S, Lee H J, Zhang L, Higgins G A, Parker E M (2004) Chronic treatment with the gamma-secretase inhibitor LY-411, 575 inhibits beta-amyloid peptide production and alters lymphopoiesis and intestinal cell differentiation. Journal of Biological Chemistry. 279 (13):12876-12882; Milano J, McKay J, Dagenais C, Foster-Brown L, Pognan F, Gadient R, Jacobs R T, Zacco A, Greenberg B, Ciaccio P J (2004) Modulation of notch processing by gamma-secretase inhibitors causes intestinal goblet cell metaplasia and induction of genes known to specify gut secretory lineage differentiation. Toxicological Sciences. 82(1):341-358; van Es J H, van Gijn M E, Riccio O, van den Born M, Vooijs M, Begthel H, Cozijnsen M, Robine S, Winton D J, Radtke F, Clevers H (2005) Notch/gamma-secretase inhibition turns proliferative cells in intestinal crypts and adenomas into goblet cells. Nature. 435(7044):959-963). In addition, Notch function appears to be critical for the proper differentiation of T and B lymphocytes (Hadland B K, Manley N R, Su D, Longmore G D, Moore C L, Wolfe M S, Schroeter E H, Kopan R (2001) Gamma-secretase inhibitors repress thymocyte development. Proceedings of the National Academy of Sciences. 98(13):7487-7491; Doerfler P, Shearman M S, Perlmutter R M (2001) Presenilin-dependent gamma-secretase activity modulates thymocyte development. Proceedings of the National Academy of Sciences. 98(16):9312-9317). Thus, pharmacologically targeting γ-secretase activity requires agents that selectively block Aβ while minimally inhibiting activity towards Notch.

The present invention provides a novel class of cyclobutyl sulfone derivatives which inhibit the processing of APP by the putative γ-secretase while sparing Notch signaling pathway, and thus are useful in the treatment or prevention of AD.

SUMMARY OF THE INVENTION

The invention encompasses a novel class of cyclobutyl sulfone derivatives which inhibit the processing of APP by the putative γ-secretase while sparing Notch signaling pathway, and thus are useful in the treatment or prevention of Alzheimer's disease without the development of Notch inhibition mediated gastrointestinal issues. Pharmaceutical compositions and methods of use are also included.

DETAILED DESCRIPTION OF THE INVENTION

Figure 1:
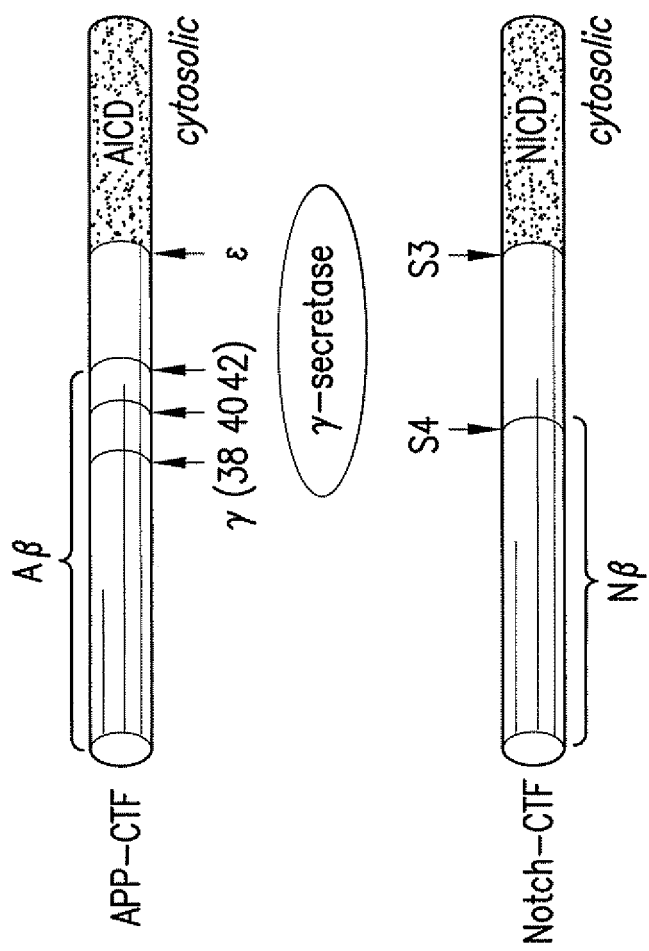
FIG. 1. γ-Secretase cleaves APP and Notch at two main positions approximately in the middle of the membrane (γ/S4-cleavage) and at the cytosolic face of the membrane (ε/S3-cleavage). The ε/S3-cleavage is a critical processing event since it liberates the intracellular domain (ICD) of the substrate from the membrane: AICD and NICD, respectively. This step is prerequisite for ICD translocation to the nucleus and its subsequent function as transcriptional modulator. On the other hand, the γ/S4-cleavage leads to the release of Aβ peptides and Aβ-like peptides (Nβ) from APP and Notch, respectively. The latter cleavage has mainly generated attention since it produces the C terminus of the Aβ peptide, which is believed to be the disease-causing agent for AD.

The invention encompasses a genus of compounds according to Formula I

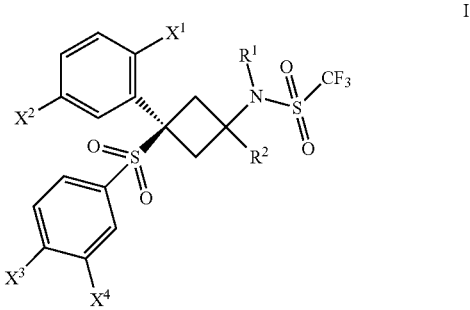

or pharmaceutically acceptable salt thereof, wherein:
$X^1$ is selected from the group consisting of: F and CN;
$X^2$ is selected from the group consisting of: F, Cl and CN;
$X^3$ is selected from the group consisting of: F, Br, Cl, CN, $CF_3$, $OCF_3$, $C(O)$—$OCH_3$ and S—$CH_3$;
$X^4$ is selected from the group consisting of: H, F and Cl;
$R^1$ is selected from the group consisting of:
 (a) H,
 (b) $CH_3$,
 (c) —$(CH_2)_n$—$OR^3$;
 (d) —$(CH_2)_n$—$C(O)$—$OR^4$ and
 (e) —$SO_2$—$CF_3$;
$R^2$ is H or $CH_3$ when the compound of formula I is in the cis configuration, otherwise $R^2$ is H;

R³ is a five- or six-membered non-aromatic heterocycle having one oxygen heteroatom;
R⁴ is H or CH₃; and
n is 1 to 4.

Within the genus, the invention encompasses a first subgenus of compounds of Formula Ia

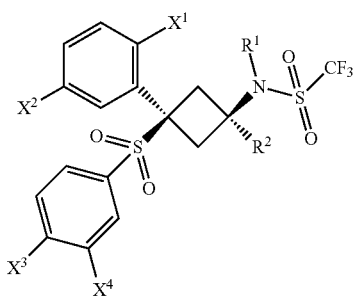

or a pharmaceutically acceptable salt thereof.

Within the first subgenus, the invention encompasses a first class of compounds of formula Ia wherein:
X¹ is F and
X⁴ is H.

Within the first class, the invention encompasses a subclass of compounds of formula Ia wherein:
X² is F and
X³ is Cl.

Within the sub-class, the invention encompasses a group of compounds of formula Ia wherein R² is H.

Also within the group, the invention encompasses a second sub-group of compounds of formula Ia wherein R¹ is —(CH₂)$_n$—C(O)—OR⁴.

Within the genus, the invention encompasses a second sub-genus of compounds of Formula Ib

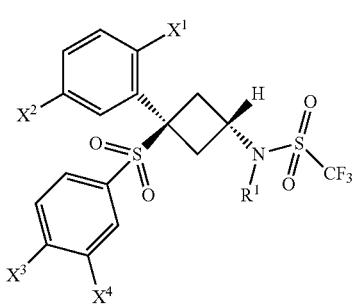

or a pharmaceutically acceptable salt thereof.

Within the second sub-genus, the invention encompasses a second class of compounds of formula Ib wherein:
X¹ and X² are F;
X³ is Cl; and
X⁴ is H.

The invention also encompasses any of the examples that follow.

The invention also encompasses a pharmaceutical composition comprising a compound according to formula I or a pharmaceutically acceptable salt thereof and a pharmaceutically acceptable carrier.

The invention also encompasses a method of treatment of a subject suffering or prone to a condition associated with the deposition of β-amyloid which comprises administering to that subject an effective amount of a compound according to formula I or a pharmaceutically acceptable salt thereof.

The invention also encompasses the use of a compound according to formula I or a pharmaceutically acceptable salt thereof for the manufacture of a medicament for treating or preventing Alzheimer's disease.

Where a variable occurs more than once in formula I or in a substituent thereof, the individual occurrences of that variable are independent of each other, unless otherwise specified.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be emphasized that the invention, for each compound in accordance with formula I, encompasses both enantiomeric forms, either as homochiral compounds or as mixtures of enantiomers in any proportion. In an embodiment of the invention, the compound of formula I is a homochiral compound of formula Ia or formula Ib, or a pharmaceutically acceptable salt thereof. Where the compounds according to the invention possess two or more asymmetric centres, they may additionally exist as diastereoisomers. It is to be understood that all such isomers and mixtures thereof in any proportion are encompassed within the scope of the present invention.

It will also be appreciated that where more than one isomer can be obtained from a reaction then the resulting mixture of isomers can be separated by conventional means. Where the processes for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), polyvinylpyrrolidone) or gelatin.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

The following examples illustrate the present invention. Where they are not commercially available, the starting materials and reagents used in the synthetic schemes may be prepared by conventional means. The invention also encompasses a compound selected from the examples that follow.

During any of the synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

EXAMPLES

Intermediate A

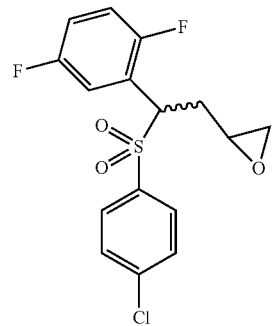 [SMILES: O=S(=O)(c1ccc(Cl)cc1)C(CC1CO1)c1cc(F)ccc1F]

2-[2-[(4-chlorophenyl)sulfonyl]-2-(2,5-difluorophenyl)ethyl]oxirane 4-chlorophenyl-2,5-difluorobenzylsulfone was prepared as described in WO 02/081435 (Intermediate 1) from 4-chlorothiophenol and 2,5-difluorobenzyl bromide in two steps.

4-chlorophenyl-2,5-difluorobenzylsulfone (12 g, 39.6 mmol) in THF (99 ml) was treated with "BuLi (19 ml, 2.5 M in hexane, 47.6 mmol) at 0° C. for 10 min followed by addition of epichlorohydrin (3.73 ml, 47.6 mmol). The reaction was slowly warmed to room temperature for 14 h, quenched with water (100 ml) and diluted with EtOAc (300 ml). The organic phase was separated, dried ($Na_2SO_4$) and evaporated to dryness to give an oil. This material was chromatographed on silica, eluting with 10-45% ethyl acetate in hexanes to afford 9.8 g of the desired product as off-white solid. $^1$H NMR (600 MHZ, $CDCl_3$) two diastereomers (~1/1) δ 7.52 (m, 2H/2H), 7.38 (m, 2H/2H), 7.30-7.22 (m, 1H/1H), 6.99 (m, 1H/1H), 6.86-6.80 (m, 1H/1H), 4.76-4.70 (m, 1H/1H), 3.03-

2.48 (m, 4H/4H), 2.37 (m, 1H), 2.20 (m, 1H). MS calculated 359.0 (MH+), exp 358.9 (MH+).

Intermediate B

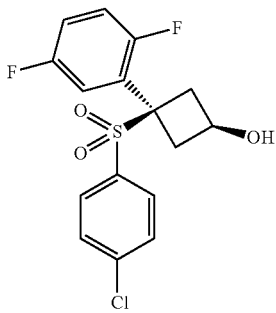 [SMILES: O=S(=O)(c1ccc(Cl)cc1)[C@]1(c2cc(F)ccc2F)C[C@H](O)C1]

cis-3-[(4-chlorophenyl)sulfonyl]-3-(2,5-difluorophenyl)cyclobutanol

To 2-[2-[(4-chlorophenyl)sulfonyl]-2-(2,5-difluorophenyl)ethyl]oxirane (100 mg, 0.279 mmol) in THF (2.7 ml) was added MeMgBr (279 μL, 3M in ether, 0.836 mmol) at −78° C. The reaction was warmed to room temperature over 1 h then quenched with sat. NH4Cl (3 ml) and diluted with EtOAc (10 ml). The organic phase was washed with brine (10 ml), dried (Na2SO4) and evaporated to dryness to afford the desired product (100 mg). $^1$H NMR (600 MHZ, CDCl3) δ 7.66 (d, J=8.4 Hz, 2H), 7.57 (d, J=8.4 Hz, 2H), 6.99 (m, 1H), 6.82 (m, 1H), 6.74 (m, 1H), 4.28 (m, 1H), 3.47 (d, J=11.4 Hz, 1H, OH), 3.13 (m, 4H). MS calculated 422.0 (MNa++CH3CN), exp 421.9 (MNa++CH3CN).

Intermediate C

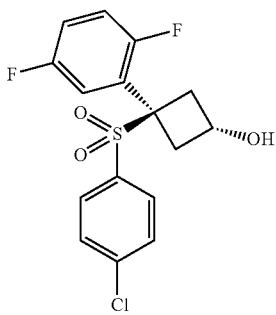

trans-3-[(4-chlorophenyl)sulfonyl]-3-(2,5-difluorophenyl)cyclobutanol

To PPh3 (8.19 g, 31.2 mmol) in THF (100 ml) was added DIAD (6.31 g, 31.2 mmol); the resulting mixture was stirred at room temperature for 0.5 h. The mixture was cooled to −50° C. and cis-3-[(4-chlorophenyl)sulfonyl]-3-(2,5-difluorophenyl)cyclobutanol (8 g, 22.3 mmol) in THF (10 ml) was added. The reaction was stirred for 20 min followed by addition of solid 4-nitrobenzoic acid (5.22 g, 31.2 mmol). The resulting mixture was warmed to room temperature and allowed to stir at room temperature for 20 h. The reaction was then cooled to 0° C. to which was added NaOMe (134 ml, 0.5 M in MeOH, 66.9 mmol). After 40 min the reaction was quenched with Sat. NH4Cl (100 ml) and diluted with EtOAc (300 ml). The organic phase was separated, dried (Na2SO4) and evaporated to dryness to afford an oil. This material was chromatographed on silica, eluting with ether in hexanes to give 8 g of the title product as white solid containing ~15% of cis-3-[(4-chlorophenyl)sulfonyl]-3-(2,5-difluorophenyl)cyclobutanol (starting material). $^1$H NMR (600 MHZ, CDCl3) major product, δ 7.35 (m, 4H), 6.96 (m, 1H), 6.80-6.72 (m, 2H), 4.84 (m, 1H), 3.49 (m, 2H), 2.59 (m, 2H). MS calculated 422.0 (MNa++CH3CN), exp 421.9 (MNa++CH3CN).

Intermediate D

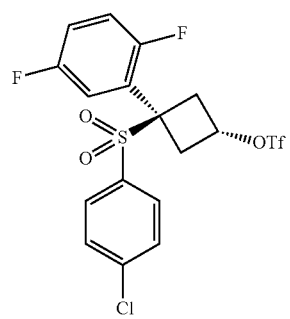

trans-3-[(4-chlorophenyl)sulfonyl]-3-(2,5-difluorophenyl)cyclobutyl trifluoromethanesulfonate To trans-3-[(4-chlorophenyl)sulfonyl]-3-(2,5-difluorophenyl)cyclobutanol (2 g, 5 mmol) in DCM (27.9 ml) was added trifluoromethanesulfonic anhydride (1.13 ml, 6.69 mmol) and pyridine (0.902 ml, 11.15 mmol) at 0° C. The reaction was stirred for 30 min, quenched with Sat. NH4Cl (30 ml) and diluted with EtOAc (150 ml). The organic phase was separated, dried (Na2SO4) and evaporated to dryness to give an oil. This material was chromatographed on silica, eluting with 0-25% ethyl acetate in hexanes to afford 2.7 g of the desired product as white solid, $^1$H NMR (600 MHZ, CDCl3) δ 7.36 (m, 4H), 7.02 (m, 1H), 6.79 (m, 2H), 5.72 (m, 1H), 3.66 (broad s, 2H), 3.02 (dd, J=14.4, 6.6 Hz, 2H). MS calculated 554.0 (MNa++CH3CN), exp 553.8 (MNa++CH3CN).

Intermediate E

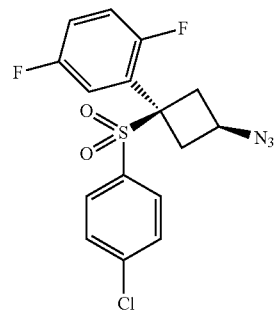 [SMILES: [N-]=[N+]=N[C@H]1C[C@@](c2cc(F)ccc2F)(S(=O)(=O)c2ccc(Cl)cc2)C1]

cis-3-azido-1-(2,5-difluorophenyl)cyclobutyl 4-chlorophenyl sulfone

A mixture of trans-3-[(4-chlorophenyl)sulfonyl]-3-(2,5-difluorophenyl)cyclobutyl trifluoromethanesulfonate (3.9 g, 7.95 mmol) and sodium azide (5.17 g, 79 mmol) in ethanol (39.7 ml) and water (39.7 ml) was heated at 85° C. for 2 h. The mixture was cooled to room temperature and diluted with water (100 ml) and EtOAc (150 ml). The organic phase was separated, dried ($Na_2SO_4$) and evaporated to dryness to afford an oil. This material was chromatographed on silica, eluting with 0-30% ethyl acetate in hexanes to afford the desired 2.3 g product as white solid, $^1$H NMR (600 MHZ, $CDCl_3$) δ 7.35 (m, 4H), 7.02 (m, 1H), 6.91 (m, 1H), 6.80 (m, 1H), 3.81 (m, 1H), 3.30 (m, 2H), 3.02 (m, 2H).

Intermediate F

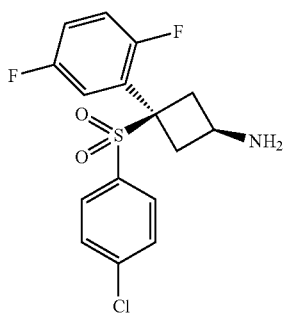 [SMILES: N[C@H]1C[C@@](c2cc(F)ccc2F)(S(=O)(=O)c2ccc(Cl)cc2)C1]

cis-3-[(4-chlorophenyl)sulfonyl]-3-(2,5-difluorophenyl)cyclobutanamine cis-3-Azido-1-(2,5-difluorophenyl)cyclobutyl 4-chlorophenyl sulfone (2.07 g, 5.39 mmol) and palladium (0.861 g, 10% on carbon, 0.809 mmol) in MeOH (27 ml) was stirred under $H_2$ balloon for 4 h. The crude mixture was filtered through a silica gel pack and washed with 5:1 DCM/MeOH (100 ml) to remove palladium residue. The solvent was removed to give the product which was used directly in next transformation without further purification. $^1$H NMR (600 MHZ, $CDCl_3$) δ 7.34 (m, 4H), 6.97 (m, 1H), 6.84 (m, 1H), 6.77 (m, 1H), 3.45 (m, 1H), 3.05-2.94 (m, 4H). MS calculated 358.0 ($MH^+$), exp 358.0 ($MH^+$).

Method (b)

To a solution of cis-3-azido-1-(2,5-difluorophenyl)cyclobutyl 4-chlorophenyl sulfone (9.5 g, 24.75 mmol) in ethanol/THF stirred at RT was added zinc (3.24 g, 49.5 mmol), followed by ammonium formate (3.12 g, 49.5 mmol). Reaction was stirred at room temperature for 1 h. The mixture was filtered through Celite and their solvents were removed. To the resulting residue was added 100 ml of sat'd NaHCO3 solution and the products was extracted with EtOAc (2×100 ml). Combined organics were washed with brine and dried over anhydrous sodium sulfate, and filtered through Celite. The filtrate was concentrated to afford the desired product Intermediate G

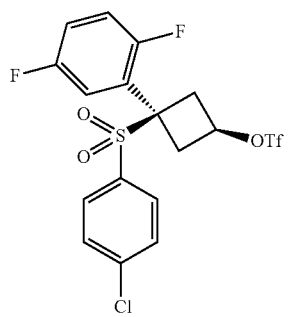

cis-3-[(4-chlorophenyl)sulfonyl]-3-(2,5-difluorophenyl)cyclobutyl trifluoromethanesulfonate Prepared as for trans-3-[(4-chlorophenyl)sulfonyl]-3-(2,5-difluorophenyl)cyclobutyl trifluoromethanesulfonate, using cis-3-[(4-chlorophenyl)sulfonyl]-3-(2,5-difluorophenyl)cyclobutanol:
$^1$H NMR (600 MHZ, $CDCl_3$) δ 7.35 (m, 4H), 7.04 (m, 1H), 6.88 (m, 1H), 6.81 (m, 1H), 5.08 (m, 1H), 3.60 (m, 2H), 3.23 (m, 2H). MS calculated 554.0 ($MNa^+$+$CH_3CN$), exp 553.8 ($MNa^+$+$CH_3CN$).

Intermediate H

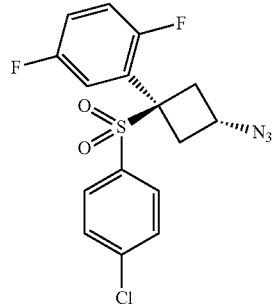 [SMILES: [N-]=[N+]=N[C@H]1C[C@](c2cc(F)ccc2F)(S(=O)(=O)c2ccc(Cl)cc2)C1]

trans-3-azido-1-(2,5-difluorophenyl)cyclobutyl 4-chlorophenyl sulfone

Prepared as for cis-3-azido-1-(2,5-difluorophenyl)cyclobutyl 4-chlorophenyl sulfone, using cis-3-[(4-chlorophenyl)sulfonyl]-3-(2,5-difluorophenyl)cyclobutyl trifluoromethanesulfonate.
$^1$H NMR (600 MHZ, $CDCl_3$) δ 7.35 (m, 4H), 6.98 (m, 1H), 6.76 (m, 2H), 4.56 (m, 1H), 3.49 (m, 2H), 2.66 (m, 2H).

Intermediate I

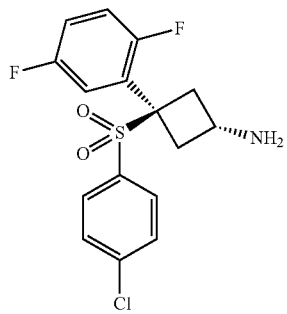 [SMILES: N[C@H]1C[C@](c2cc(F)ccc2F)(S(=O)(=O)c2ccc(Cl)cc2)C1]

trans-3-[(4-chlorophenyl)sulfonyl]-3-(2,5-difluorophenyl)cyclobutanamine

Prepared as for cis-3-[(4-chlorophenyl)sulfonyl]-3-(2,5-difluorophenyl)cyclobutanamine, using trans-3-azido-1-(2,5-difluorophenyl)cyclobutyl 4-chlorophenyl sulfone.

$^1$H NMR (600 MHZ, CD$_3$OD) δ 7.48-7.41 (m, 4H), 7.07 (m, 1H), 6.88 (m, 1H), 6.79 (m, 1H), 3.88 (m, 1H), 3.41 (m, 2H), 2.50 (m, 2H). MS calculated 358.0 (MH$^+$), exp 358.0 (MH$^+$).

Intermediate J

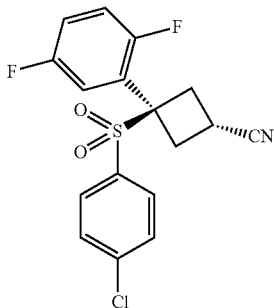

trans-3-[(4-chlorophenyl)sulfonyl]-3-(2,5-difluorophenyl)cyclobutanecarbonitrile cis-3-[(4-chlorophenyl)sulfonyl]-3-(2,5-difluorophenyl)cyclobutyl trifluoromethanesulfonate (4 g, 8.15 mmol) and tetrabutylammonium cyanide (5.47 g, 20.37 mmol) in DMSO (54 ml) was heated at 80° C. for 45 min. The resulting mixture was cooled to room temperature and diluted with water (200 ml) and EtOAc (250 ml). The organic phase was washed with water, brine, separated, dried (Na$_2$SO$_4$) and evaporated to dryness, to afford an oil. This material was chromatographed on silica, eluting with 0-50% ethyl acetate in hexanes to give the desired product (2.9 g) as off-white solid. $^1$H NMR (600 MHZ, CDCl$_3$) δ 7.38-7.33 (m, 4H), 7.02 (m, 1H), 6.80-6.74 (m, 2H), 3.74 (m, 1H), 3.51 (m, 2H), 3.02 (m, 2H). MS calculated 431.0 (MNa$^+$+CH$_3$CN), exp 431.0 (MNa$^+$+CH$_3$CN).

Intermediate K

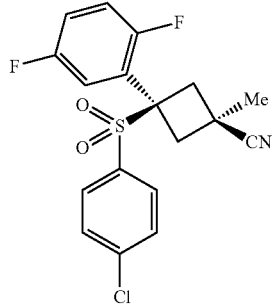 [SMILES: C[C@]1(C#N)C[C@@](c2cc(F)ccc2F)(S(=O)(=O)c2ccc(Cl)cc2)C1]

cis-3-[(4-chlorophenyl)sulfonyl]-3-(2,5-difluorophenyl)-1-methylcyclobutanecarbonitrile To trans-3-[(4-chlorophenyl)sulfonyl]-3-(2,5-difluorophenyl)cyclobutanecarbonitrile (600 mg, 1.63 mmol) in THF (8 mL) was added LiHMDS (2.45 ml, 1 M in THF, 2.45 mmol) at −78° C. After 10 min MeI (306 μl, 4.89 mmol) was introduced to reaction mixture. The reaction was stirred for 2 h with the temperature slowly increasing to 0° C. The reaction was then quenched with water and extracted with EtOAc. The organic phase was separated, dried (Na$_2$SO$_4$) and evaporated to dryness to afford an oil. This material was chromatographed on silica, eluting with 0-50% ethyl acetate in hexanes to give the product (260 mg) as a single diastereomeric products. $^1$H NMR (600 MHZ, CD$_3$OD) δ 7.36 (s, 4H), 7.02 (m, 1H), 6.85-6.78 (m, 2H), 3.79 (d, J=14.4 Hz, 2H), 2.72 (d, J=14.4 Hz, 2H), 1.44 (s, 3H). MS calculated 785.1 (2M+Na$^+$), exp 785.0 (2M+Na$^+$).

Intermediate L

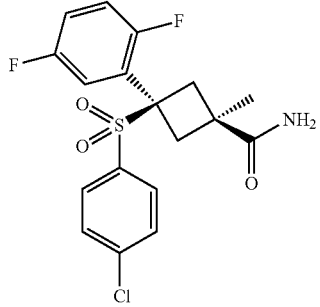 [SMILES: C[C@]1(C(N)=O)C[C@@](c2cc(F)ccc2F)(S(=O)(=O)c2ccc(Cl)cc2)C1]

cis-3-[(4-chlorophenyl)sulfonyl]-3-(2,5-difluorophenyl)-1-methylcyclobutanecarboxamide To cis-3-[(4-chlorophenyl)sulfonyl]-3-(2,5-difluorophenyl)-1-methylcyclobutanecarbonitrile (500 mg, 1.31 mmol) and K$_2$CO$_3$ (362 mg, 2.62 mmol) in DMSO (6.5 ml) was added H$_2$O$_2$ (1.15 ml, 35% in water, 13.1 mmol) dropwise and the reaction was stirred vigorously for 2 h. The mixture was diluted with water (50 ml) and EtOAc (50 ml). The organic phase was washed with water, brine, separated, dried (Na$_2$SO$_4$) and evaporated to dryness to give cis-3-[(4-chlorophenyl)sulfonyl]-3-(2,5-difluorophenyl)-1-methylcyclobutanecarboxamide (500 mg) as off-white solid which was used in the next reaction without further purification. $^1$NMR (600 MHZ, CDCl$_3$) δ 7.35 (m, 4H), 7.02 (m, 1H), 6.87-6.79 (m, 2H), 6.54 (broad s, 1H), 6.40 (broad s, 1H), 3.67 (d, J=14.4 Hz, 2H), 2.62 (d, J=14.4 Hz, 2H), 1.28 (s, 3H). MS calculated 400.0 (MH$^+$), exp 400.0 (MH$^+$).

Intermediate M

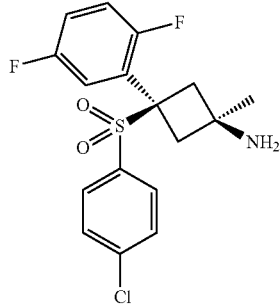 [SMILES: C[C@]1(N)C[C@@](c2cc(F)ccc2F)(S(=O)(=O)c2ccc(Cl)cc2)C1]

cis-3-[(4-chlorophenyl)sulfonyl]-3-(2,5-difluorophenyl)-1-methylcyclobutanamine cis-3-[(4-chlorophenyl)sulfonyl]-3-(2,5-difluorophenyl)-1-methylcyclobutanecarboxamide (400 mg, 1 mmol) and PIFA (473 mg, 1.1 mmol) in acetonitrile (2.5 ml) and water (2.5 ml) was stirred at 0° C. and the mixture was slowly warmed up to room temperature over 27 h. The reaction was then quenched with Sat. NaHCO$_3$ and extracted with EtOAc. The organic phase was separated, dried (Na$_2$SO$_4$) and evaporated to dryness to give an oil. This material was chromatographed on silica, eluting with 0-40% MeOH in DCM to give cis-3-[(4-chlorophenyl)sulfonyl]-3-(2,5-difluorophenyl)-1-methylcyclobutanamine (380 mg) as product. $^1$H NMR (600 MHZ, CD$_3$OD) δ 7.41-7.36 (m, 4H), 7.02 (m, 1H), 6.81 (m, 1H), 6.74 (m, 1H), 3.58 (d, J=15.6 Hz, 2H), 2.89 (d, J=15.6 Hz, 2H), 1.58 (s, 3H). MS calculated 372.1 (MH$^+$), exp 372.0 (MH$^+$).

Intermediate N

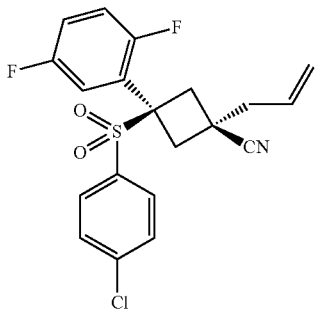 [SMILES: C=CC[C@]1(C#N)C[C@@](c2cc(F)ccc2F)(S(=O)(=O)c2ccc(Cl)cc2)C1]

cis-1-allyl-3-[(4-chlorophenyl)sulfonyl]-3-(2,5-difluorophenyl)cyclobutanecarbonitrile Prepared as for cis-3-[(4-chlorophenyl)sulfonyl]-3-(2,5-difluorophenyl)-1-methylcyclobutanecarbonitrile, using trans-3-[(4-chlorophenyl)sulfonyl]-3-(2,5-difluorophenyl)cyclobutanecarbonitrile
and allyl bromide.

$^1$H NMR (600 MHZ, CDCl$_3$) δ 7.36 (s, 4H), 7.03 (m, 1H), 6.83-6.78 (m, 2H), 5.70 (m, 1H), 5.18 (dd, J=10.2, 1.2 Hz, 1H), 5.07 (dd, 1H, J=16.8, 1.2 Hz, 1H), 3.70 (d, J=15.0 Hz, 2H), 2.77 (d, J=15.0 Hz, 2H), 2.32 (d, J=6.6 Hz, 2H). MS calculated 837.1 (2M+Na$^+$), exp 837.0 (2M+Na$^+$).

Intermediate O

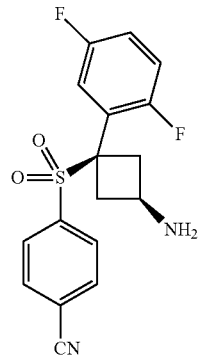 [SMILES: N#Cc1ccc(S(=O)(=O)[C@]2(c3cc(F)ccc3F)C[C@H](N)C2)cc1]

4-{[cis-3-amino-1-(2,5-difluorophenyl)cyclobutyl]sulfonyl}benzonitrile

Zinc cyanide (0.295 g, 2.52 mmol), Pd$_2$(dba)$_3$ (0.384 g, 0.419 mmol), Zinc (0.030 g, 0.461 mmol), DPPF (0.465 g, 0.838 mmol) and cis-3-[(4-chlorophenyl)sulfonyl]-3-(2,5-difluorophenyl)cyclobutanamine (1.5 g, 4.19 mmol) were taken up in DMA and stirred in a 25 mL Schlenk tube under an argon environment at 135° C. for 16 hours. Water was then added and the mixture was extracted with EtOAc. The organic layer was washed with a saturated NaHCO$_3$ solution and brine then dried over MgSO$_4$, filtered and concentrated. The residue was purified via silica column chromatography (0->8% MeOH/DCM) to give the title compound. MS: cal'd 349 (MH+), exp 349 (MH+)

Example 1

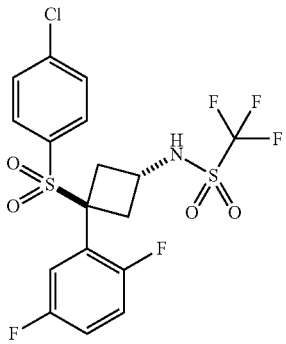

N-[trans-3-[(4-chlorophenyl)sulfonyl]-3-(2,5-difluorophenyl)cyclobutyl]-1,1,1-trifluoromethanesulfonamide To cis-3-[(4-chlorophenyl)sulfonyl]-3-(2,5-difluorophenyl)cyclobutanamine (1.5 g, 4.19 mmol) in DCM (27.9 ml) was added triethylamine (1.169 ml, 8.38 mmol) and trifluoromethanesulfonic anhydride (0.850 ml, 5.03 mmol) at 0° C. and the mixture was stirred for 2 h.

The mixture diluted with water (50 ml) and EtOAc (100 ml). The organic phase was washed with brine, separated, dried (Na$_2$SO$_4$) and evaporated to dryness to afford an oil. This material was chromatographed on silica, eluting with ethyl acetate in hexanes to give the desired product (1.45 g as white solid). $^1$H NMR (600 MHZ, CDCl$_3$) δ 7.39 (d, J=9.0 Hz, 2H), 7.34 (d, J=9.0 Hz, 2H), 7.02 (m, 1H), 6.77 (m, 2H), 4.22 (m, 1H), 3.23 (m, 4H). MS calculated 553.0 (MNa$^+$+CH$_3$CN), exp 553.0 (MNa$^+$+CH$_3$CN).

Example 2

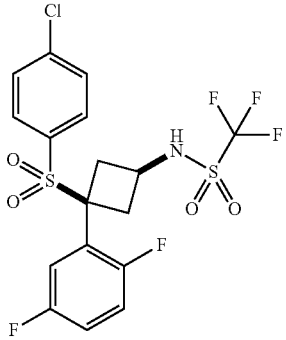

N-[cis-3-[(4-chlorophenyl)sulfonyl]-3-(2,5-difluorophenyl)cyclobutyl]-1,1,1-trifluoromethanesulfonamide Prepared as for Example 1, using trans-3-[(4-chlorophenyl)sulfonyl]-3-(2,5-difluorophenyl)cyclobutanamine.

$^1$H NMR (600 MHZ, CDCl$_3$) δ 7.33 (m, 4H), 6.98 (m, 1H), 6.74 (m, 2H), 5.35 (d, J=7.8 Hz, 1H, NH), 4.67 (m, 1H), 3.59 (m, 2H), 2.68 (m, 2H). MS calculated 553.0 (MNa$^+$+CH$_3$CN), exp 552.8 (MNa$^+$+CH$_3$CN).

The following were prepared by similar procedures:

| # | Structure | Name | MS | Salt form |
|---|-----------|------|----|-----------| 
| 3 | 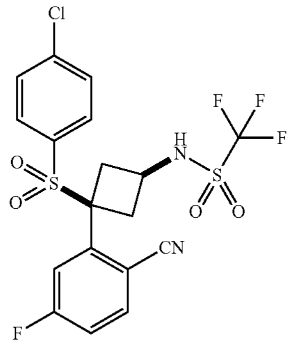 | N-[cis-3-[(4-chlorophenyl)sulfonyl]-3-(2-cyano-5-fluorophenyl)cyclobutyl]-1,1,1-trifluoromethanesulfonamide | Cal'd 519.0 (MNa+), exp 519.0. | Free base |
| 4 | 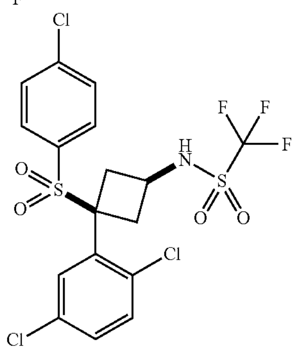 | N-[cis-3-[(4-chlorophenyl)sulfonyl]-3-(2,5-dichlorophenyl)cyclobutyl]-1,1,1-trifluoromethanesulfonamide | Cal'd 543.9 (MNa+), exp 543.9. | Free base |
| 5 | 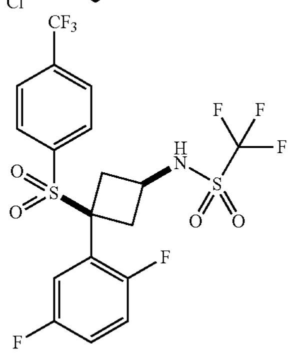 | N-(cis-3-(2,5-difluorophenyl)-3-{[4-(trifluoromethyl)phenyl]sulfonyl}-cyclobutyl)-1,1,1-trifluoromethanesulfonamide | Cal'd 546 (MNa+), exp 546. | Free base |

Example 6

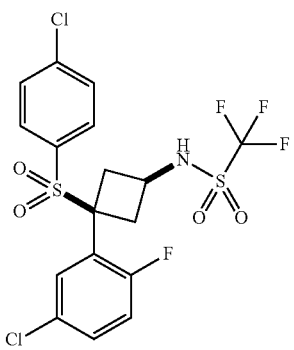

N-{cis-3-(5-chloro-2-fluorophenyl)-3-[(4-chlorophenyl)sulfonyl]cyclobutyl}-1,1,1-trifluoromethanesulfonamide MS Cal'd 506 (MNa+), exp 529; $^1$H NMR (400 MHz, CDCl$_3$) δ 7.41~7.43 (d, J=8.8 Hz, 2H), 7.34~7.36 (d, J=8.4 Hz, 2H), 7.28~7.33 (m, 1H), 6.98~7.01 (m, 1H), 6.75~6.83 (m, 2H), 4.20~4.29 (m, 1H), 3.20~3.32 (m, 4H).

Example 7

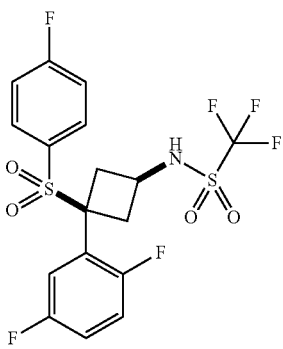

N-{cis-3-(2,5-difluorophenyl)-3-[(4-fluorophenyl)sulfonyl]cyclobutyl}-1,1,1-trifluoromethanesulfonamide ¹H NMR (400 MHz, CDCl₃): δ 7.45~7.49 (m, 2H), 7.12~7.29 (m, 2H), 7.04~7.10 (m, 1H), 6.80~6.85 (m, 3H), 4.24~4.30 (m, 1H), 3.24~3.35 (m, 4H).

Example 8

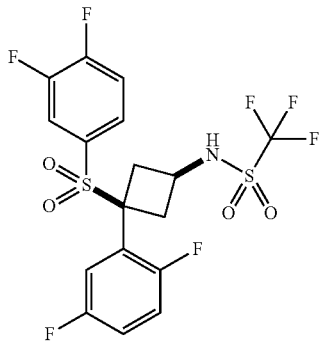

N-{cis-3-(2,5-difluorophenyl)-3-[(3,4-difluorophenyl)sulfonyl]cyclobutyl}-1,1,1-trifluoromethanesulfonamide MS Cal'd 514 (MH+), exp 514; ¹H NMR (400 MHz, CDCl₃): δ 7.15~7.19 (m, 3H), 6.97~7.04 (m, 1H), 6.72~6.80 (m, 2H), 6.63~6.65 (d, J=10.4 Hz, H), 4.13~4.23 (m, 1H), 3.14~3.26 (m, 4H).

Example 9

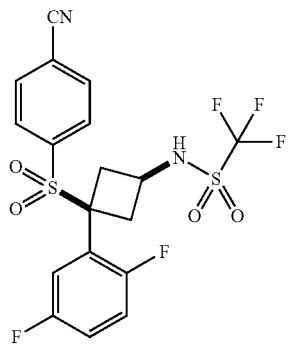

N-[cis-3-[(4-cyanophenyl)sulfonyl]-3-(2,5-difluorophenyl)cyclobutyl]-1,1,1-trifluoromethanesulfonamide MS: cal'd 502 (MNa+), exp 502 (MNa+). ¹H NMR (CDCl₃ 600 MHz) 7.67 (d, J=4.1 Hz, 2H), 7.58 (d, J=4.1, 2H), 7.08 (bin, 1H), 6.84 (m, 1H), 6.68 (m, 1H), 6.60 (d, 1H), 4.24 (bin, 1H), 3.4-3.2 (bm, 4H)

Intermediate P

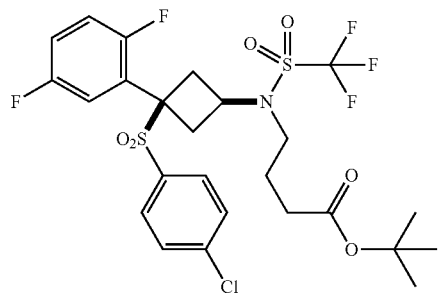 [SMILES: CC(C)(C)OC(=O)CCCN([C@H]1C[C@@](c2cc(F)ccc2F)(S(=O)(=O)c2ccc(Cl)cc2)C1)S(=O)(=O)C(F)(F)F]

Tert-Butyl 4-{[3-[(4-chlorophenyl)sulfonyl]-3-(2,5difluorophenyl)cyclobutyl][(trifluoromethyl)sulfonyl]amino}butanoate N-[cis-3-[(4-chlorophenyl)sulfonyl]-3-(2,5-difluorophenyl)cyclobutyl]-1,1,1-trifluoromethanesulfonamide (190 mg, 0.388 mmol) was added to DMF (1.1 mL) and treated with potassium carbonate (59 mg, 0.427 mmol), tert-butyl 4-bromobutanoate (95 mg, 0.427 mmol). The mixture was heated to 80° C. and stirred for 16 hours. The reaction was cooled to ambient temperature, diluted with ethyl acetate, and washed with ½ saturated brine solution twice. The organic layer was dried over anhydrous magnesium sulfate, filtered then concentrated in vacuo. The residue was purified by MPLC (0-30% EtOAc:Hept) to give the title compound. MS: cal'd 654 (M Na+), exp 654 (M Na+)

Example 10

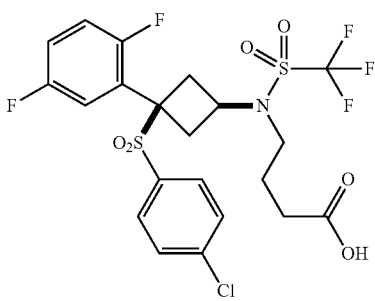 [SMILES: O=C(O)CCCN([C@H]1C[C@@](c2cc(F)ccc2F)(S(=O)(=O)c2ccc(Cl)cc2)C1)S(=O)(=O)C(F)(F)F]

4-{[cis-3-[(4-chlorophenyl)sulfonyl]-3-(2,5-difluorophenyl)cyclobutyl][(trifluoromethyl)sulfonyl]amino}butanoic acid Tert-Butyl 4-{[3-[(4-chlorophenyl)sulfonyl]-3-(2,5-difluorophenyl)cyclobutyl][(trifluoromethyl)sulfonyl]amino}butanoate (144 mg, 0.228 mmol) was added to 1:1 DCM:TFA (1.1 mL) and stirred at ambient temperature for 40 minutes. The reaction mixture was concentrated in vacuo. The title compound was isolated as a white solid after trituration with heptane. ¹H NMR (DMSO D₆, 600 MHz) δ 12.25

(s, 1H), 7.58 (d, J=8.2 Hz, 2H), 7.43 (d, J=8.2 Hz, 2H), 7.25-7.31 (m, 1H), 7.07-7.16 (m, 2H), 4.18-4.28 (m, 1H), 3.53 (s br, 2H), 3.30-3.42 (m, 2H), 3.08 (s br, 2H), 2.26-2.38 (m, 2H), 1.80-1.90 (m, 2H). MS: cal'd 598 (M Na+), exp 598 (M Na+).

1H), 3.50-4.00 (m, 7H), 2.80-3.10 (m, 2H), 1.20-1.90 (m, 7H). MS: cal'd 640 (M Na+), exp 640 (M Na+)

Example 11

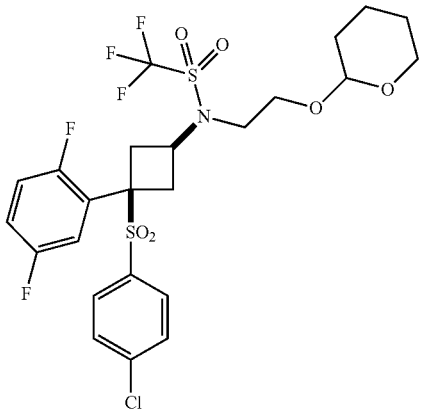 [SMILES: O=S(=O)(N(CCOC1CCCCO1)[C@H]1C[C@@](c2cc(F)ccc2F)(S(=O)(=O)c2ccc(Cl)cc2)C1)C(F)(F)F]

N-[cis-3-[(4-chlorophenyl)sulfonyl]-3-(2,5-difluorophenyl)cyclobutyl]-1,1,1-trifluoro-N-[2-(tetrahydro-2-pyran-2-yloxy)ethyl]methanesulfonamide N-[cis-3-[(4-chlorophenyl)sulfonyl]-3-(2,5-difluorophenyl)cyclobutyl]-1,1,1-trifluoromethanesulfonamide (50 mg, 0.102 mmol) was dissolved in anhydrous DMF (0.3 mL) and to this stirring solution was added potassium carbonate (49 mg, 0.357 mmol) followed by 2-(2-bromoethoxy)tetrahydro-2H-pyran (53 mg, 0.255 mmol). The resulting mixture was stirred at 80° C. for 16 hours. The mixture was cooled to ambient temperature, diluted with water, and extracted with EtOAc. The organic layer was again washed with saturated aqueous bicarbonate solution, then dried over anhydrous magnesium sulfate and concentrated in vacuo. The extract was purified by MPLC (0-45% EtOAc/DCM) to give the title compound. Rf=0.71 in 40% EtOAc/DCM. $^1$H NMR (CDCl$_3$, 600 MHz) δ 7.31-7.38 (m, 4H), 7.00-7.07 (m, 2H), 6.88-6.93 (m, 1H), 6.78-6.84 (m, 1H), 4.65-4.68 (m, 1H), 4.06-4.08 (m,

Example 12

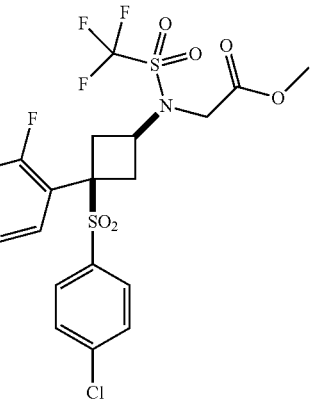

Methyl {[cis-3-[(4-chlorophenyl)sulfonyl]-3-(2,5-difluorophenyl)cyclobutyl][(trifluoromethyl)sulfonyl]amino}acetate Anhydrous THF (0.8 mL) was added to N-[cis-3-[(4-chlorophenyl)sulfonyl]-3-(2,5-difluorophenyl)cyclobutyl]-1,1,1-trifluoromethanesulfonamide (200 mg, 0.408 mmol) and the reaction was then cooled to 0° C. Sodium hydride (49 mg, 1.225 mmol) was added in one portion and the mixture was stirred at 0° C. for 15 minutes. The mixture effervesced and stirred as an off white suspension. After 15 minutes methyl bromoacetate (187 mg, 1.225 mmol) was added and the mixture effervesced again as it turned yellow. The mixture was stirred for 16 hours then quenched with saturated aq ammonium chloride and extracted with EtOAc. The organic layer was again washed with saturated aq ammonium chloride then dried over anhydrous magnesium sulfate and concentrated in vacuo. The extract was purified by MPLC (0-45% EtOAc:Hept) to give the title compound. Rf=0.6 in 40% EtOAc:Hept. $^1$H NMR (CDCl$_3$, 600 MHz) δ 7.36 (d, J=7.0 Hz, 2H), 7.43 (d, J=7.0 Hz, 2H), 7.02-7.08 (m, 1H), 6.86-6.90 (m, 1H), 6.78-6.84 (m, 1H), 4.30-4.60 (m, 3H), 3.85 (s, 3H), 3.38-3.34 (m, 2H), 3.04 (s br, 2H). MS: cal'd 584 (M Na+), exp 584 (M Na+)

The following list of compounds was prepared by similar procedures:

| # | Structure | Name | MS | Salt form |
|---|-----------|------|-----|-----------|
| 13 | 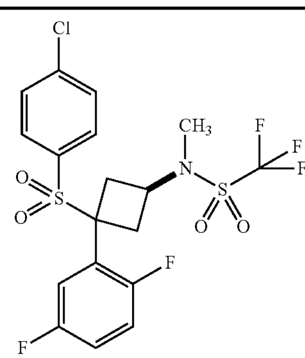 | N-[3-[(4-chlorophenyl)sulfonyl]-3-(2,5-difluorophenyl)cyclobutyl]-1,1,1-trifluoro-N-methylmethanesulfonamide | Cal'd 526.0 (MNa+), exp 525.8 (MNa+) | Free base |

-continued

| # | Structure | Name | MS | Salt form |
|---|---|---|---|---|
| 14 | 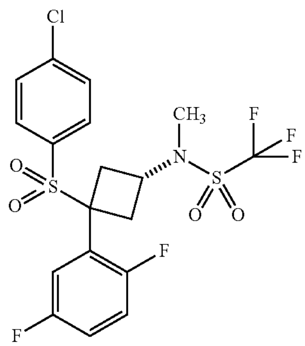 | N-[3-[(4-chlorophenyl)sulfonyl]-3-(2,5-difluorophenyl)cyclobutyl]-1,1,1-trifluoro-N-methylmethanesulfonamide | Cal'd 567.0 (MNa$^+$ + MeCN), exp 566.8 (MNa$^+$ + MeCN). | Free base |
| 15 | 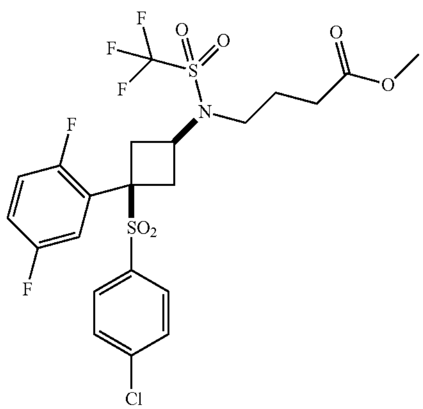 [SMILES: COC(=O)CCCN([C@H]1C[C@@](c2cc(F)ccc2F)(S(=O)(=O)c2ccc(Cl)cc2)C1)S(=O)(=O)C(F)(F)F] | methyl 4-{[cis-3-[(4-chlorophenyl)sulfonyl]-3-(2,5-difluorophenyl)cyclobutyl][(trifluoromethyl)sulfonyl]amino}butanoate | Cal'd 612.0 (MNa+), exp 612.0 | Free base |
| 16 | 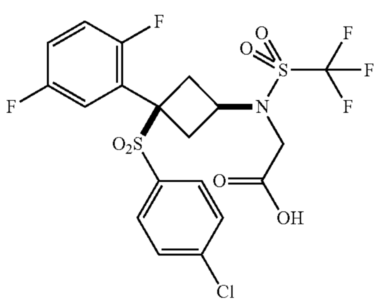 [SMILES: O=C(O)CN([C@H]1C[C@@](c2cc(F)ccc2F)(S(=O)(=O)c2ccc(Cl)cc2)C1)S(=O)(=O)C(F)(F)F] | N-[cis-3-[(4-chlorophenyl)sulfonyl]-3-(2,5-difluorophenyl)cyclobutyl]-N-[(trifluoromethyl)sulfonyl]glycine | Cal'd 570 (MNa+), exp 570. | Free base |

Example 17

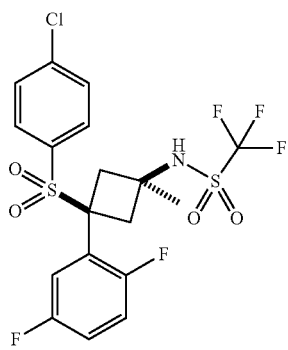

N-[cis-3-[(4-chlorophenyl)sulfonyl]-3-(2,5-difluorophenyl)-1-methylcyclobutyl]-1,1,1-trifluoromethanesulfonamide Prepared as for Example 1, using cis-3-[(4-chlorophenyl)sulfonyl]-3-(2,5-difluorophenyl)-1-methylcyclobutanamine.
$^1$H NMR (600 MHZ, CDCl$_3$) δ 7.33 (m, 4H), 7.00 (m, 1H), 6.90 (s, 1H, NH), 6.82-6.75 (m, 2H), 3.54 (d, J=14.4 Hz, 2H), 2.87 (d, J=14.4 Hz, 2H), 1.44 (s, 3H). MS calculated 526.0 (MNa$^+$), exp 525.9 (MNa$^+$).

Example 18

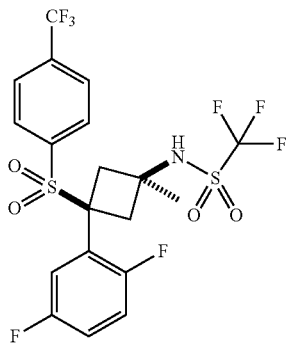

N-(cis-3-(2,5-difluorophenyl)-1-methyl-3-{[4-(trifluoromethyl)phenyl]sulfonyl}cyclobutyl)-1,1,1-trifluoromethanesulfonamide Prepared using procedures similar to example 17. Calcd (2M+Na)+: 1097.0. Found: 1096.5.

Example 19

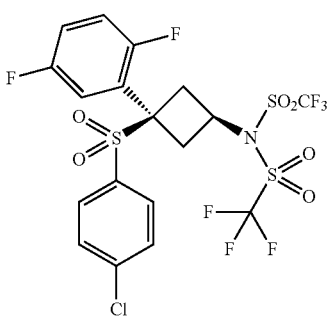

N-[cis-3-[(4-chlorophenyl)sulfonyl]-3-(2,5-difluorophenyl)cyclobutyl]-1,1,1-trifluoro-N-[(trifluoromethyl)sulfonyl]methanesulfonamide Prepared in Example 1 synthesis as byproduct.
$^1$H NMR (600 MHZ, CDCl$_3$) δ 7.38-7.33 (m, 4H), 7.07 (m, 1H), 6.95 (m, 1H), 6.84 (m, 1H), 4.44 (m, 1H), 182 (m, 2H), 3.15 (m, 2H). MS calculated 684.9 (MNa$^+$+CH$_3$CN), exp 684.9 (MNa$^+$+CH$_3$CN).

Example 20

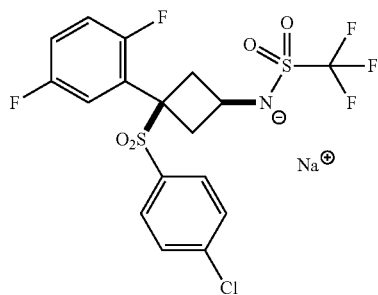 [SMILES: O=S(=O)([N-][C@H]1C[C@@](c2cc(F)ccc2F)(S(=O)(=O)c2ccc(Cl)cc2)C1)C(F)(F)F ; [Na+]]

Sodium [cis-3-[(4-chlorophenyl)sulfonyl]-3-(2,5-difluorophenyl)cyclobutyl][(trifluoromethyl)sulfonyl]azanide Sodium hydride was suspended in hexane and cooled to 0° C. N-[cis-3-[(4-chlorophenyl)sulfonyl]-3-(2,5-difluorophenyl)cyclobutyl]-1,1,1-trifluoromethanesulfonamide (200 mg, 0.408 mmol) in THF (1 mL) was added dropwise to the sodium hydride suspension. The resulting mixture was stirred at 0° C. for 15 minutes then at ambient temperature for 30 minutes. At which time, the reaction mixture was concentrated in vacuo. A dry white powder was scraped out of the flask, placed in a glass fritted funnel and washed with ice cold pentane (45 mL). The powder was then placed under high vacuum for 16 hours. $^1$H NMR (DMSO D$_6$, 600 MHz) δ 7.56 (d, J=8.5 Hz, 2H), 7.33 (d, J=8.5 Hz, 2H), 7.20-7.26 (m, 1H), 7.00-7.12 (m, 2H), 3.42-3.52 (m, 1H), 2.66-2.80 (m, 4H).

Example 21

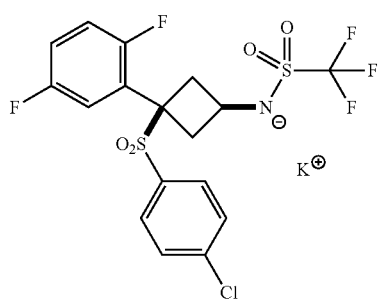 [SMILES: O=S(=O)([N-][C@H]1C[C@@](c2cc(F)ccc2F)(S(=O)(=O)c2ccc(Cl)cc2)C1)C(F)(F)F ; [K+]]

Potassium [cis-3-[(4-chlorophenyl)sulfonyl]-3-(2,5-difluorophenyl)cyclobutyl][(trifluoromethyl)sulfonyl]azanide N-[cis-3-[(4-chlorophenyl)sulfonyl]-3-(2,5-difluorophenyl)cyclobutyl]-1,1,1-trifluoromethanesulfonamide (1.2 g, 2.55 mmol) was stirred in anhydrous THF (25.5 mL) at 0° C. and then treated with potassium tert-butoxide (0.29 g, 2.55 mmol). The reaction mixture was stirred at 0° C. for 15 minutes then warmed to ambient temperature and stirred for another 45 minutes. After the reaction was concentrated in vacuo, the resultant white powder was recrystallized from a minimal amount of 3:1 IPA:Toluene (400 mL) stirring at 100° C. Once in solution the mixture was filtered through paper and allowed to sit undisturbed at 4° C. for 20 hours. Crystals were harvested by filtration through a glass frit, and washed with cold pentane three times. Residual solvent was removed under vacuum. $^1$H NMR (DMSO D$_6$, 600 MHz) δ 7.56 (d, J=8.5 Hz, 2H), 7.33 (d, J=8.5 Hz, 2H), 7.20-7.26 (m, 1H), 7.00-7.12 (m, 2H), 3.42-3.52 (m, 1H), 2.66-2.80 (m, 4H).

Example 22

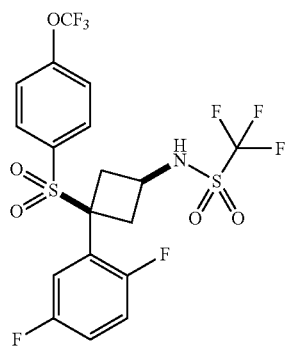

N-[cis-3-[(4-trifluoromethoxyphenyl)sulfonyl]-3-(2,5-difluorophenyl)cyclobutyl]-1,1,1-trifluoromethanesulfonamide Prepared as for Example 2, using cis-3-[(4-trifluoromethoxyphenyl)sulfonyl]-3-(2,5-difluorophenyl)cyclobutanamine.

$^1$H NMR (600 MHZ, CDCl$_3$) δ 7.56 (m, 2H), 7.27 (m, 2H) 7.088 (m, 1H), 6.78 (m, 2H), 6.68 (d, J=10.6 Hz, 1H, NH), 4.30 (m, 1H), 3.31 (m, 2H), 3.18 (m, 2H). MS calculated 603.46 (MNa$^+$+CH$_3$CN), exp 603.0 (MNa$^+$+CH$_3$CN).

Biological Activity

Assays to determine the biological activity of the compounds of the invention are described as follows:

APP Processing (Assay Quantitates Secreted Aβ Analytes from Cell Lines):

The effect of compounds on the abundance of Aβ40 and Aβ42 peptides generated from SH-SY5Y cells expressing amyloid β protein (SP4CT cells) was determined by an AlphaLisa™ assay. Analogous to an ELISA assay, generation of signal in this AlphaLisa™ assay requires "donor" and "acceptor" beads to be brought in close proximity by specific antibody recognition of either Aβ40 or Aβ42 peptides. The assay was accomplished by removing media from compound-treated SP4CT cells to two different microplates, followed by the addition of donor beads conjugated with streptavidin binding a biotinylated anti-amyloid β monoclonal antibody (clone 4G8). Acceptor beads directly conjugated with anti-Aβ40 monoclonal antibody (G210) were added to one microplate and anti-Aβ42 monoclonal antibody (12F4) acceptor beads were added to the other. Abundance of Aβ40 and Aβ42 was directly proportional to the luminescent signal generated following excitation of donor beads by laser light.

Notch Processing: (Assay Quantitates Notch Intracellular Domain Release in Cell Lines):

A "split-luciferase" assay is used to measure inhibition of gamma secretase-dependent cleavage of the Notch protein. In this assay, HeLa cells were made to express a Notch protein lacking its extracellular domain (NotchΔE) fused to an N-terminal fragment of luciferase. The same cells also expressed a C-terminal fragment of luciferase fused to the immunoglobulin J kappa recombination signal sequence binding protein (RBP). Upon NotchΔE cleavage by gamma secretase, a Notch intracellular domain (NICD)-N terminal luciferase protein is generated which translocates to the nucleus and binds the RBP-C terminal luciferase fusion, bringing two independently nonfunctional halves of luciferase together to form a functional luciferase enzyme. The activity of luciferase in these cells is directly proportional to the amount of gamma secretase-cleaved Notch. Luciferase activity is determined by the standard techniques of luciferin addition to lysed cells and measurement of total luminescence.

PXR Assay Description

The CYP3A4-SEAP transactivation assay (PCSTA) effectively and rapidly evaluates compounds for their potential to induce cytochrome P450 CYP3A (human CYP3A4 or rat CYP3A1). The reporter construct contains regulatory regions from the CYP3A4 gene positioned just upstream of a secreted alkaline phosphatase (SEAP) gene. The human PXR nuclear receptor has been modified at the 5'-end so that methionine is the initiating amino acid replacing leucine found in the wild-type sequence. HEP G2 cells are transfected with the PXR plasmid (human or rat) and the reporter plasmid. Read-out for the induction of CYP3A4 consists of a SEAP calorimetric assay with para-nitro-phenyl phosphate (pNPP) as the substrate. Five point dose-response curves in duplicate are then generated with each point corresponding to the rate of conversion of pNPP to pNP by SEAP. For the human PCSTA, rifampicin is used as the positive control and 100% induction is based upon the maximum induction produced by rifampicin at 10 μM.

ICD Transactivation (Assay Quantitates Intracellular Domain Release of a Panel of γ-Secretase Substrates in Cell Lines)

A Firefly luciferase based transactivation assay is used to measure inhibition of ε/S3-site cleavage of γ-secretase substrates. This assay involves the use of chimeric substrates harboring a GAL4/VP16 (GVP) transactivation domain fused to the intracellular domain (ICD): APP-GVP, NotchΔE-GVP, E-cadherin-GVP and CD44-GVP. Upon cleavage and release of ICDs, the GVP domain drives the expression of the luciferase gene under the control of the UAS promoter. In this assay, HEK cells were transiently co-transfected with the chimeric substrate along with a UAS promoter driven luciferase and β-galactosidase (transfection control). Upon cleavage by γ-secretase, the released ICD-GVP translocates to the nucleus to drive the expression of the UAS-luciferase gene. The activity of luciferase in these cells is directly proportional to the amount of γ-secretase-cleaved ICDs. Luciferase activity is determined by the standard techniques of luciferin addition to lysed cells and measurement of total luminescence. In addition, to account for the differences in transfection efficiencies an absorbance based β-galactosidase enzyme assay is performed to normalize the luminescence read-out.

Assessing Full Length γ-Secretase Substrates (Assay Qualitatively Assesses the Processing of a Panel of γ-Secretase Substrates)

To examine the effect of compounds on γ-secretase activity against other substrates, four HEK 293 stable cell lines overexpressing one of the following type I membrane proteins: CD43, CD44, E-Cadherin and SCN2b with a C-terminal V5 tag, were generated. Cells are plated and treated overnight with titrated compound and the phorbol ester, TPA. Since all of the proteins undergo regulated membrane proteolysis characterized by an initial ectodomain shedding event followed by the intramembraneous cleavage of the C-teen final fragment (CTF) by γ-secretase, TPA induces the initial cleavage event producing the substrate for γ-secretase. The effect of compounds on γ-secretase activity in relation to these substrates is measured by tracking the processing of the V5 tagged CTFs by Western blot analysis. Accumulation of the CTFs indicates inhibition of γ-secretase activity.

ICD Transactivation (Assay Quantitates Intracellular Domain Release of a Panel of γ-Secretase Substrates in Cell Lines)

A Firefly luciferase based transactivation assay is used to measure inhibition of ε/S3-site cleavage of γ-secretase substrates. This assay involves the use of chimeric substrates harboring a GAL4/VP16 (GVP) transactivation domain fused to the intracellular domain (ICD): APP-GVP, NotchΔE-GVP, E-cadherin-GVP and CD44-GVP. Upon cleavage and release of ICDs, the GVP domain drives the expression of the luciferase gene under the control of the UAS promoter. In this assay, HEK cells were transiently co-transfected with the chimeric substrate along with a UAS promoter driven luciferase and β-galactosidase (transfection control). Upon cleavage by γ-secretase, the released ICD-GVP translocates to the nucleus to drive the expression of the UAS-luciferase gene. The activity of luciferase in these cells is directly proportional to the amount of γ-secretase-cleaved ICDs. Luciferase activity is determined by the standard techniques of luciferin addition to lysed cells and measurement of total luminescence. In addition, to account for the differences in transfection efficiencies an absorbance based β-galactosidase enzyme assay is performed to normalize the luminescence read-out.

In Vitro APP Processing (Assay Quatitates Aβ Analytes Generated from a Recombinant APPC100Flag Substrate Incubated with Semi-Purified γ-Secretase)

The effect of compounds on the abundance of Aβ40 and Aβ42 peptides generated from exogenous C100Flag substrate by semi-purified γ-secretase was determined by MESO Scale ELISA. Generation of signal in this MESO Scale assay requires an anti-amyloid monoclonal antibody (clone 4G8) conjugated with streptavidin to bind to a biotin-coated plate. Specific [Ru(bpy)3]2+-labeled monoclonal antibodies for either Aβ40 (G210) or Aβ42 (12F4) subsequently generate an electrochemiluminescence signal upon electrochemical stimulation. The assay was accomplished by incubating compound, C100Flag substrate and CHAPSO-solubilized P2 membranes from HeLa cells or brains of mouse, rat, or dog. The reaction was then transferred to two different biotinylated microplates for detection of either Aβ40 or Aβ42.

In Vitro Notch Processing (Assay Qualitatively Assess Notch Intracellular Domain Generation from Recombinant NotchΔE100Flag Substrate Incubated with Semi-Purified γ-Secretase)

In an analogous manner, Notch processing can be monitored using the same method as the C100Flag in vitro assay but by substituting substrate for N100Flag. A polyclonal biotin-conjugated anti-DYKDDDDK antibody was used as capture antibody while a polyclonal [Ru(bpy)3]2+-labeled cleaved Notch1 antibody was used to detect NICD.

Compound Binding: (Assay Quantitates In Vitro Displacement of Bound γ-Secretase Inhibitor Tracers)

All radioligand binding experiments are performed using CHAPSO-solubilized HEK293 (gammaNRCF8) P2 membranes stably over expressing recombinant gamma secretase. For radioligand binding, solubilized enzyme is incubated in the presence of tritiated inhibitors. Nonspecific binding is determined by adding an excess of unlabeled inhibitor to the reaction, and serial dilutions of the tritiated ligands are used to obtain saturation binding isotherm. Bound ligand is separated from free ligand by adsorption of the enzyme complex to polyethyleneimine-coated glass fiber filter plates and rapid filtration in a cell harvester followed by washing. After drying plates, scintillant is added, and the plates are read on a Microplate Scintillation counter. Binding competition assay is performed by incubating serial dilutions of various inhibitors in the presence of 1 nM $^3$H-labeled compound Reference Example L-458 (transition state inhibitor) or 4 nM $^3$H-labeled compound Reference Example L-881 (non-transition state inhibitor). To determine the antagonist competitiveness of various inhibitors, respective $^3$H tracer doss-response curves are analyzed in presence of different concentrations of these compounds.

Reference Example L-458

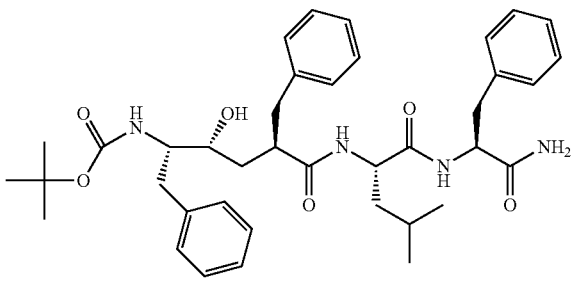 [SMILES: CC(C)C[C@H](NC(=O)[C@H](Cc1ccccc1)C[C@@H](O)[C@H](Cc1ccccc1)NC(=O)OC(C)(C)C)C(=O)N[C@@H](Cc1ccccc1)C(N)=O]

Reference Example L-881

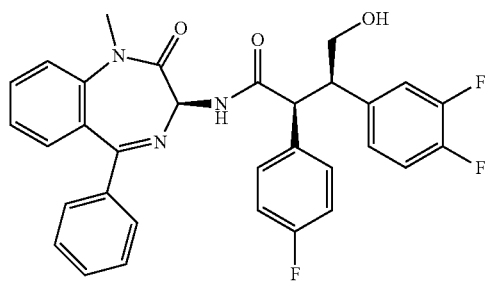 [SMILES: CN1C(=O)[C@@H](NC(=O)[C@H](c2ccc(F)cc2)[C@@H](CO)c2ccc(F)c(F)c2)N=C(c2ccccc2)c2ccccc21]

Results

The examples herein were tested in the APP and Notch processing cell based functional assays described above. The tested compounds demonstrated in vitro inhibition of APP processing while sparing Notch signaling pathway as shown in the following table. The data is based on an average of at least >4 replicates.

| Ex. No. | AB40 IC50 AVG (nM) | AB42 IC50 AVG (nM) | Notch IC50 AVG (nM) |
|---|---|---|---|
| 1 | 151.2 | 117.3 | 50000 |
| 2 | 42.84 | 38.37 | 3485 |
| 3 | 70.08 | 66.08 | 3208 |
| 4 | 70.84 | 78.23 | 1940 |
| 5 | 100.4 | 90.21 | 3808 |
| 6 | 129.9 | 105.6 | 5645 |
| 7 | 68.37 | 57.57 | 3081 |
| 8 | 79.17 | 62.84 | 3142 |
| 9 | 260.5 | 230.6 | 8896 |
| 10 | 35.19 | 30.74 | 8315 |
| 11 | 43.42 | 36.93 | 2538 |
| 12 | 97.71 | 116.9 | 13180 |
| 13 | 18.35 | 18.9 | 4812 |
| 14 | 89.87 | 97.09 | 9865 |
| 15 | 51.78 | 51.76 | 2834 |
| 16 | 96.65 | 67.91 | 32040 |
| 17 | 37.28 | 37 | 5214 |
| 18 | 60.76 | 65.44 | 4470 |
| 19 | 62.57 | 48.7 | 5677 |
| 20 | 61.24 | 53.2 | 1769 |
| 21 | 64.93 | 70.93 | 2130 |
| 22 | 250.2 | 237.3 | 5204 |

WO 02/081435 A1, published Oct. 17, 2002, discloses sulfone derivatives that modulate the activity of gamma secretase. WO 2004/031139, published Apr. 15, 2004, discloses cyclohexyl sulfone derivatives as gamma secretase inhibitors. Example 47 of WO 2004/031139 has the following structure:

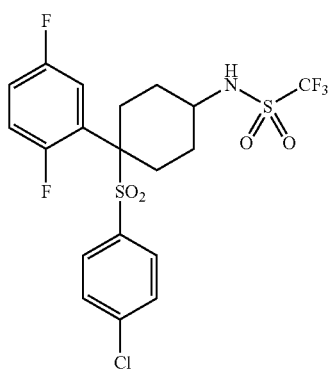 [SMILES: O=S(=O)(NC1CCC(c2cc(F)ccc2F)(S(=O)(=O)c2ccc(Cl)cc2)CC1)C(F)(F)F]

The above compound is also described as MRK-560 and disclosed in Best et al., *J. Pharmacol. Exp. Ther.*, 317:786-790, 2006 and Best et al, *J. Pharmacol. Exp. Ther.*, 320:552-558, 2007. Although the literature reports little or no separation for MRK-560 between the in vitro inhibition of the APP and Notch processing pathway, the compound did demonstrate in vivo beneficial effects on amyloid plaque deposition in the absence of toxicity related to changes in the Notch signaling pathway in the Tg2576 mouse.

MRK-560 and Example 2 were tested in a covalent protein binding assay which is predictive of drug toxicity. The potential of drug candidates to cause covalent binding to proteins is evaluated by incubation of the radiolabeled version of the compound in question with liver microsomes. A semi-automated method based on Brandel Harvester technique is then used to measure the formation of covalent adducts of the test compound to liver proteins binding (Ref. Day et. al, *J Pharmacol Toxicol Methods.* 52, 278-85, 2005). The results are shown in the table below.

| Ex. No. | covalent protein binding (human microsomes) pmol/mg |
|---|---|
| MRK-560 | 1308 |
| 2 | 380 |

MRK-560 and the examples disclosed herein were tested for their ability to bind to and/or activate the pregnane X receptor (PXR), which is predictive of drug-drug interactions. The results are shown in the following table.

| Ex. No. | PXR EC50 AVG (nM) | PXR % Activation @ 10 uM |
|---|---|---|
| MRK-560 | 617 | |
| 1 | 1219 | |
| 2 | 3433 | 55.5 |
| 3 | 713.6 | 92.3 |
| 4 | 1956 | 70.7 |
| 5 | 5201 | 64.4 |
| 6 | 1989 | 79.2 |
| 7 | 766.3 | 113.2 |
| 8 | 1256 | 82.3 |
| 9 | 8358 | 54.9 |
| 10 | 1236 | 76.7 |
| 11 | 826 | 86.5 |
| 12 | 1603 | |
| 13 | 1261 | |
| 14 | 828.8 | |
| 15 | 1206 | |
| 16 | 1011 | 100 |
| 17 | 848 | 74.6 |
| 18 | 3093 | 75.5 |
| 19 | 1246 | 89.1 |
| 20 | 2891 | 71.9 |
| 21 | 3383 | 64.4 |
| 22 | 9647 | 50.6 |

Figure 2:
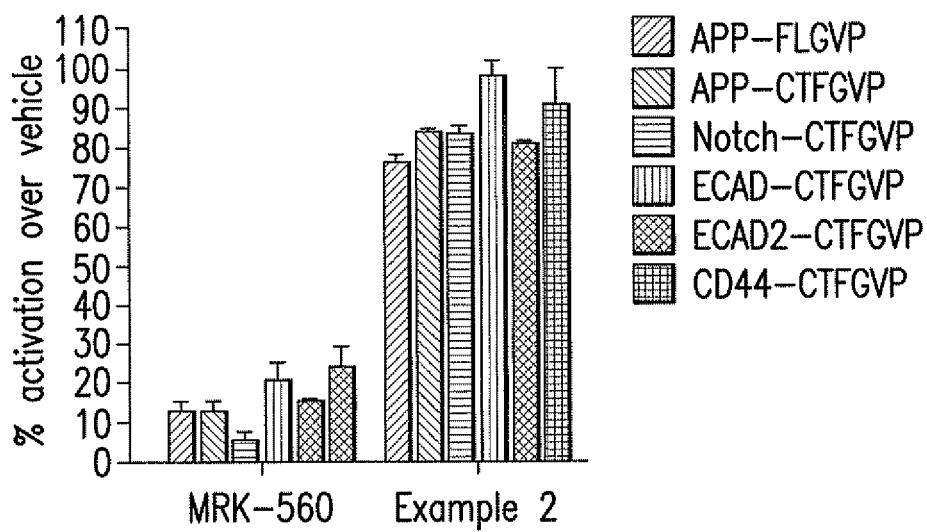
FIG. 2. Results of MRK-560 and Example 2 tested in the transactivation assay described in this application to examine the effects on the initial cleavage of other γ-secretase substrates. HEK cells were transiently co-transfected with the chimeric substrate along with a UAS promoter driven luciferase and β-galactosidase, and then treated with 1 μM of each compound for 48 hours. MRK-560 inhibited ICD release of all examined substrates, whereas Example 2 retained ICD release and subsequent translocation of the ICD-GVP construct to allow for reporter activation.

In order to examine the effects on the initial cleavage of other γ-secretase substrates, MRK-560 and Example 2 were tested in a transactivation assay described above. MRK-560 inhibited ICD release of all examined substrates, whereas Example 2 retained initial ε/S3-cleavage, as evidenced by ICD release and subsequent translocation of the ICD-GVP construct to allow for reporter activation. See FIG. 2.

Figure 3:
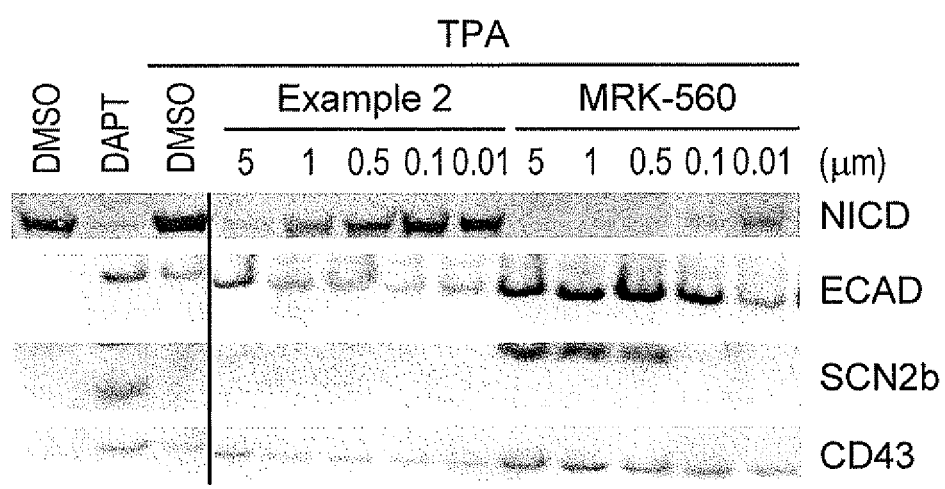
FIG. 3. HEK293 cells stably overexpressing each substrate, NotchΔE, E-cadherin, SCN2b and CD43, were treated with MRK-560 or Example 2 at titrated concentrations along with TPA to induce the shedding. Immunoblot analysis of cell lysates revealed that MRK-560 inhibited NICD generation and caused accumulation of CTFs, direct substrates of γ-secretase, in a similar manner to a traditional γ-secretaseinhibitor, DAPT. In contrast, Example 2 allowed for NICD generation and no or less CTF accumulation was observed compared MRK-560.

Cell-based multi-substrate assay confirmed full inhibition of ε/S3- and γ-cleavages by MRK-560 resulting in SCN2b-, ECAD- and CD43-CTF accumulation. In contrast, Example 2 treatment showed no or less CTF accumulation indicating that NS-GSIs spare initial cleavage of γ-secretase substrates. See FIG. 3.

Figure 4A:
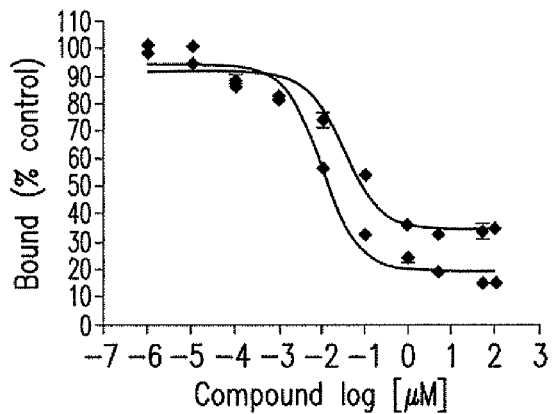
FIG. 4. The results of MRK-560 and Example 2 tested in the compound binding assay described in this application. Tritiated GSI tracers L-458 (transition state, red) or L-881 (non transition state, blue) were incubated with semi-purified γ-secretase complex and increasing concentrations of the respective compounds. A-MRK-560 showed full and partial displacement of at L-881 and L-458 sites, respectively. B-Example 2 was able to fully displace L-881 but not L-458. The results demonstrate that notch sparing compounds such as Example 2 have a shifted binding site as compared to traditional inhibitors such as MRK-560. This deregulates enzymatic cleavage in a manner that spares ε/S3 (AICD/NICD release) while potently inhibiting all γ-cleavage sites.
Figure 4B:
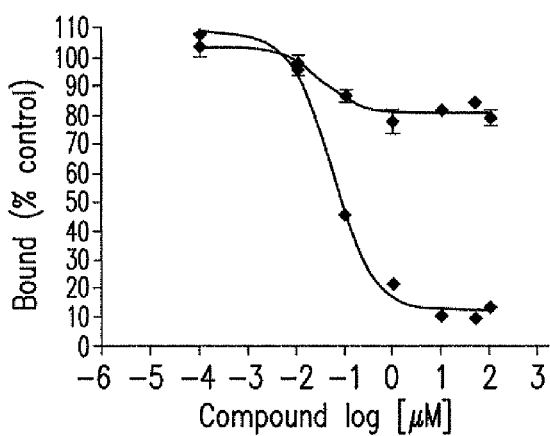

MRK-560 and Example 2 were also tested in the compound binding assay described above. Tritiated GSI tracers L-458 (transition state, red) or L-881 (non transition state, blue) were incubated with semi-purified γ-secretase complex and increasing concentrations of the respective compounds. MRK-560 showed full and partial displacement of at L-881 and L-458 sites, respectively. Example 2 was able to fully displace L-881 but not L-458. The results demonstrate that notch sparing compounds such as Example 2 have a shifted binding site as compared to traditional inhibitors such as MRK-560. This deregulates enzymatic cleavage in a manner that spares ε/S3 (AICD/NICD release) while potently inhibiting all γ-cleavage sites. See FIG. 4.

What is claimed is:

1. A compound according to Formula I

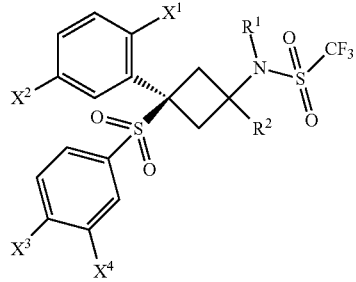

or pharmaceutically acceptable salt thereof, wherein:
$X^1$ is selected from the group consisting of: F and CN;
$X^2$ is selected from the group consisting of: F, Cl and CN;
$X^3$ is selected from the group consisting of F, Br, Cl, CN, $CF_3$, $OCF_3$, C(O)—$OCH_3$ and S—$CH_3$;
$X^4$ is selected from the group consisting of H, F and Cl;
$R^1$ is selected from the group consisting of:
   (a) H,
   (b) $CH_3$,
   (c) —$(CH_2)_n$—$OR^3$;
   (d) —$(CH_2)_n$—C(O)—$OR^4$ and
   (e) —$SO_2$—$CF_3$;
$R^2$ is H or $CH_3$ when the compound of formula I is in the cis configuration, otherwise $R^2$ is H;
$R^3$ is a five- or six-membered non-aromatic heterocycle having one oxygen heteroatom;
$R^4$ is H or $CH_3$; and
n is 1 to 4.

2. The compound according to claim 1 of Formula Ia

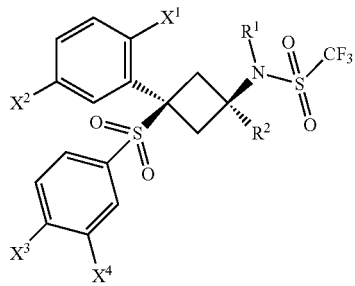

or a pharmaceutically acceptable salt thereof.

3. The compound according to claim 2 wherein:
$X^1$ is F and
$X^4$ is H.

4. The compound according to claim 3 wherein:
$X^2$ is F and
$X^3$ is Cl.

5. The compound according to claim 4 wherein $R^2$ is H.

6. The compound according to claim 5 wherein $R^1$ is —$(CH_2)_n$—C(O)—$OR^4$.

7. The compound according to claim 1 of Formula Ib

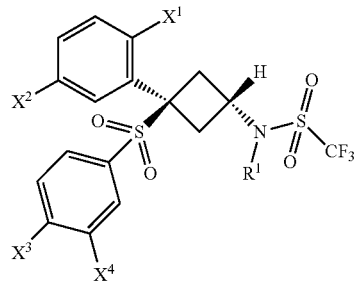

or a pharmaceutically acceptable salt thereof.

8. The compound according to claim 7 wherein:
$X^1$ and $X^2$ are F;
$X^3$ is Cl; and
$X^4$ is H.

9. A compound according to claim 1 selected from the following group:

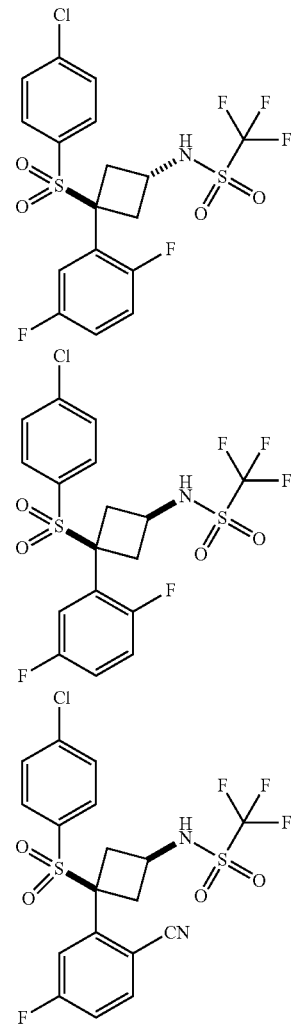

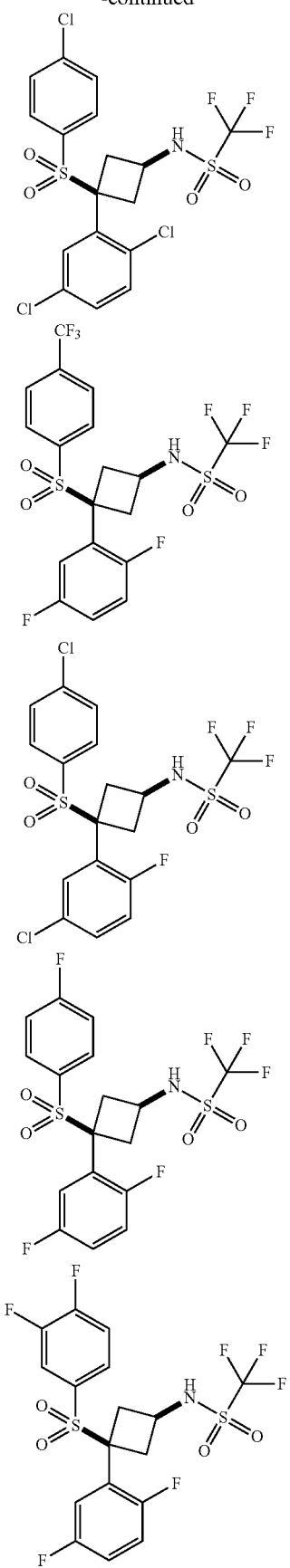
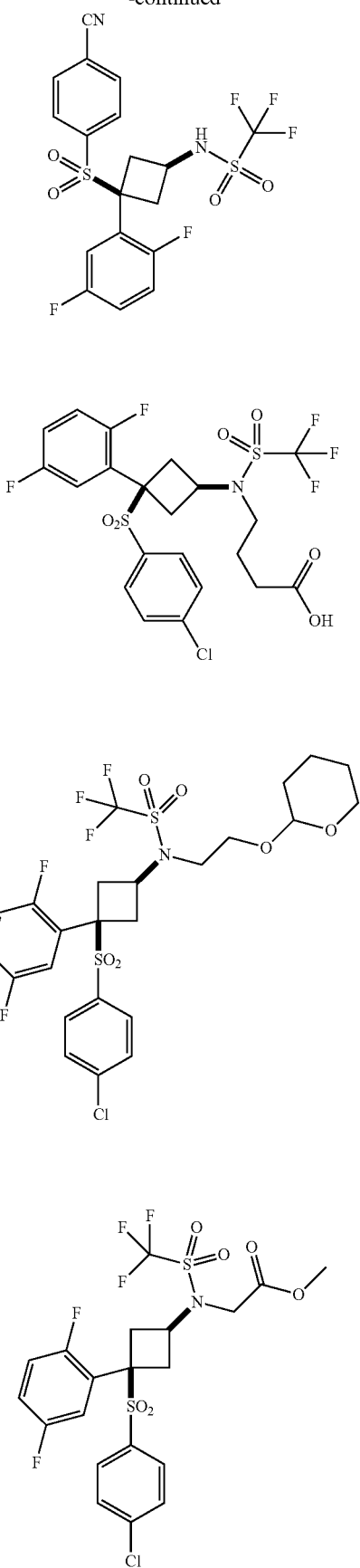

-continued
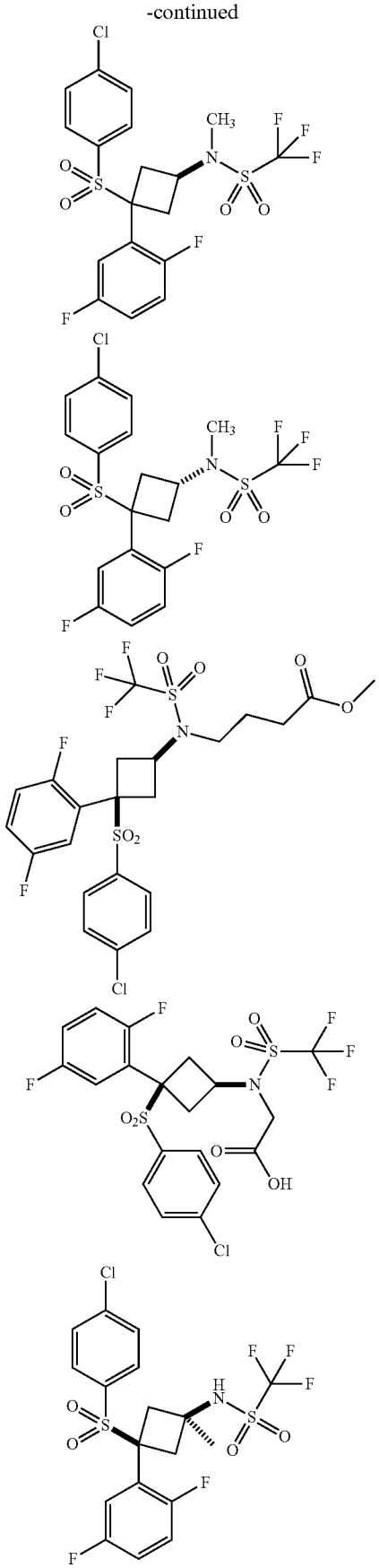
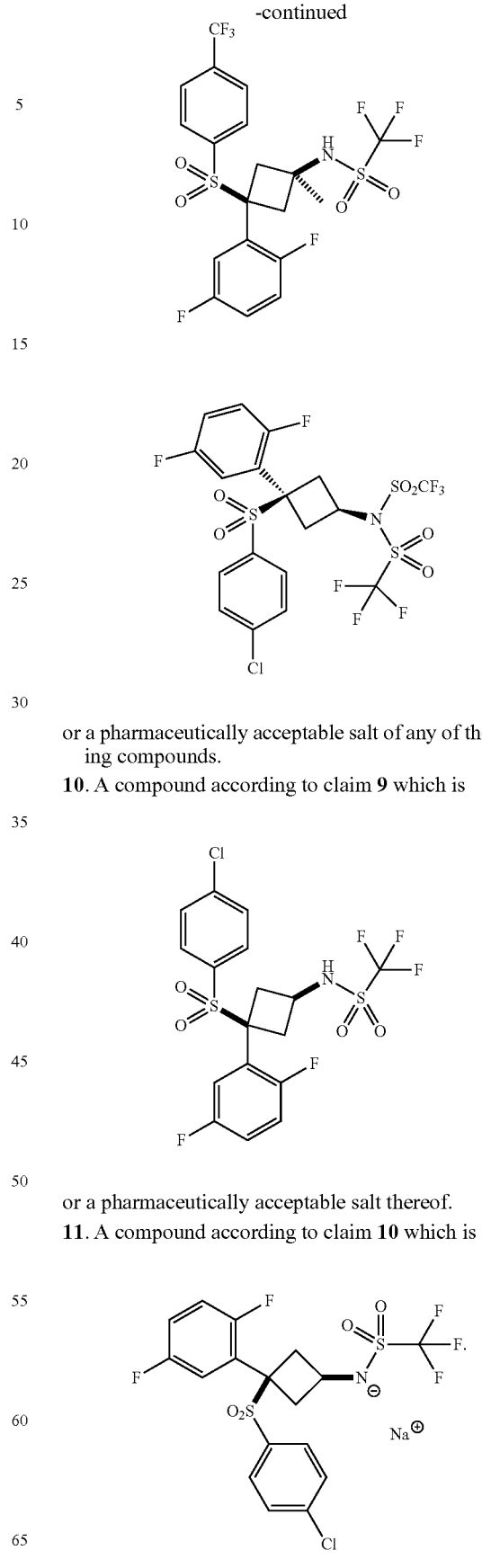
or a pharmaceutically acceptable salt of any of the foregoing compounds.
10. A compound according to claim 9 which is
or a pharmaceutically acceptable salt thereof.
11. A compound according to claim 10 which is 12. A compound according to claim 10 which is

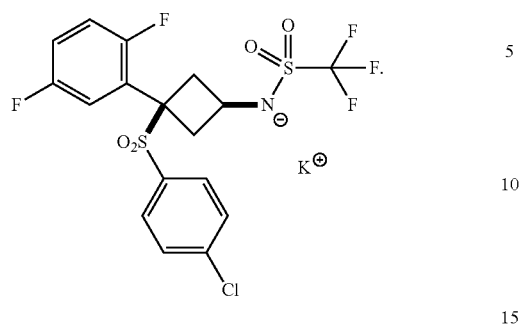

13. A pharmaceutical composition comprising a compound according to claim 1 or a pharmaceutically acceptable salt thereof and a pharmaceutically acceptable carrier.

14. A method of treatment of a subject suffering or prone to a condition associated with the deposition of β-amyloid which comprises administering to that subject an effective amount of a compound according to claim 1 or a pharmaceutically acceptable salt thereof.

* * * * *